United States Patent
Hole et al.

(10) Patent No.: US 8,079,998 B2
(45) Date of Patent: Dec. 20, 2011

(54) METHODS AND DEVICES FOR THE DELIVERY OF THERAPEUTIC GASES INCLUDING NITRIC OXIDE

(75) Inventors: Douglas R. Hole, Edmonton (CA); Curtis Figley, Edmonton (CA); Robert E. Lee, Camerose (CA); Michael Hudec, Edmonton (CA); Robert Rolfson, Tofield (CA)

(73) Assignee: Pulmonox Technologies Corporation, Edmonton (CA)

( * ) Notice: Subject to any disclaimer, the term of this patent is extended or adjusted under 35 U.S.C. 154(b) by 105 days.

(21) Appl. No.: 11/713,344

(22) Filed: Mar. 2, 2007

(65) Prior Publication Data
US 2008/0097282 A1 Apr. 24, 2008

Related U.S. Application Data

(60) Provisional application No. 60/853,103, filed on Oct. 20, 2006.

(51) Int. Cl.
*A61M 31/00* (2006.01)
(52) U.S. Cl. .......................................... 604/500; 604/23
(58) Field of Classification Search .................... 604/23, 604/24, 26, 500, 503, 505
See application file for complete search history.

(56) References Cited

U.S. PATENT DOCUMENTS

| | | | |
|---|---|---|---|
| 3,036,584 A | 5/1962 | Lee | |
| 3,192,106 A | 6/1965 | Bracken et al. | |
| 4,127,121 A | 11/1978 | Westenskow et al. | |
| 4,191,952 A | 3/1980 | Schreiber et al. | |
| 4,224,941 A | 9/1980 | Stivala | |
| 4,328,823 A | 5/1982 | Schreiber | |
| 4,336,798 A | 6/1982 | Beran | |
| 4,345,612 A | 8/1982 | Koni et al. | |
| 4,442,856 A | 4/1984 | Betz et al. | |
| 4,608,041 A | 8/1986 | Nielsen | |
| 4,611,590 A | 9/1986 | Ryschka et al. | |
| 4,770,168 A | 9/1988 | Rusz et al. | |
| 4,905,685 A | 3/1990 | Olsson et al. | |
| 4,954,526 A | 9/1990 | Keefer | |
| 5,154,697 A | 10/1992 | Loori | |
| 5,155,137 A | 10/1992 | Keefer et al. | |
| 5,159,924 A | 11/1992 | Cegielski et al. | |
| 5,197,462 A | 3/1993 | Falb et al. | |
| 5,396,882 A | 3/1995 | Zapol | |
| 5,423,313 A | 6/1995 | Olsson et al. | |

(Continued)

FOREIGN PATENT DOCUMENTS
EP 0640356 A1 3/1995

(Continued)

OTHER PUBLICATIONS

Abstract for DE 003713396A1, Nov. 1998, Zeuch et al.

(Continued)

*Primary Examiner* — Bhisma Mehta
(74) *Attorney, Agent, or Firm* — Bennett Jones LLP

(57) ABSTRACT

Gas packages for the delivery of therapeutic gases, and in particular gaseous nitric oxide (gNO) are provided herein. The gas packages comprise one or more of a gas reservoir, interface layer, sealing layer, and holding container. The interface layer regulates discharge of the therapeutic gas from the gas reservoir to the external environment. The sealing layer and/or holding container prevent evolution of the gas until the sealing layer is compromised or the holding container is opened. The gas packages and methods for using them are useful for the treatment, alleviation, and prevention of various disease and non-disease, medical and non-medical, conditions in humans and animals.

15 Claims, 12 Drawing Sheets

U.S. PATENT DOCUMENTS

| | | |
|---|---|---|
| 5,427,797 A | 6/1995 | Frostell et al. |
| 5,485,827 A | 1/1996 | Zapol et al. |
| 5,514,204 A | 5/1996 | Sheu et al. |
| 5,519,020 A | 5/1996 | Smith et al. |
| 5,531,218 A | 7/1996 | Krebs |
| 5,536,241 A | 7/1996 | Zapol |
| 5,558,083 A | 9/1996 | Bathe et al. |
| 5,570,683 A | 11/1996 | Zapol |
| 5,615,669 A | 4/1997 | Olsson et al. |
| 5,632,981 A | 5/1997 | Saavedra et al. |
| 5,648,101 A | 7/1997 | Tawashi |
| 5,650,442 A | 7/1997 | Mitchell et al. |
| 5,651,358 A | 7/1997 | Briend et al. |
| 5,676,963 A | 10/1997 | Keefer et al. |
| 5,688,236 A | 11/1997 | Gragg |
| 5,692,497 A | 12/1997 | Schnitzer et al. |
| 5,700,830 A | 12/1997 | Korthuis et al. |
| 5,713,349 A | 2/1998 | Keaney |
| 5,722,392 A | 3/1998 | Skimming et al. |
| 5,732,693 A | 3/1998 | Bathe et al. |
| 5,765,548 A | 6/1998 | Perry |
| 5,789,447 A | 8/1998 | Wink, Jr. et al. |
| 5,810,795 A | 9/1998 | Westwood |
| 5,814,666 A | 9/1998 | Green et al. |
| 5,814,667 A | 9/1998 | Mitchell et al. |
| 5,823,180 A | 10/1998 | Zapol |
| 5,834,030 A | 11/1998 | Bolton |
| 5,837,736 A | 11/1998 | Mitchell et al. |
| 5,839,433 A | 11/1998 | Higgenbottam |
| 5,840,759 A | 11/1998 | Mitchell et al. |
| 5,845,633 A | 12/1998 | Psaros |
| 5,873,359 A | 2/1999 | Zapol et al. |
| 5,885,621 A | 3/1999 | Head et al. |
| 5,904,938 A | 5/1999 | Zapol et al. |
| 5,918,596 A | 7/1999 | Heinonen |
| 5,957,880 A | 9/1999 | Igo et al. |
| 6,000,403 A | 12/1999 | Cantwell |
| 6,060,020 A | 5/2000 | Piuk et al. |
| 6,063,407 A | 5/2000 | Zapol et al. |
| 6,067,983 A | 5/2000 | Stenzler |
| 6,071,254 A | 6/2000 | Augustine |
| 6,073,627 A | 6/2000 | Sunnen |
| 6,083,209 A | 7/2000 | Marasco, Jr. |
| 6,089,229 A | 7/2000 | Bathe et al. |
| 6,103,275 A | 8/2000 | Seitz et al. |
| 6,109,260 A | 8/2000 | Bathe |
| 6,110,895 A | 8/2000 | Rodgers et al. |
| 6,125,846 A | 10/2000 | Bathe et al. |
| 6,131,572 A | 10/2000 | Heinonen |
| 6,142,147 A | 11/2000 | Head et al. |
| 6,158,434 A | 12/2000 | Lugtigheid et al. |
| 6,160,021 A | 12/2000 | Lerner et al. |
| 6,164,276 A | 12/2000 | Bathe et al. |
| 6,190,704 B1 | 2/2001 | Murrell |
| 6,200,558 B1 | 3/2001 | Saavedra et al. |
| 6,232,336 B1 | 5/2001 | Hrabie et al. |
| 6,270,779 B1 | 8/2001 | Fitzhugh et al. |
| 6,358,536 B1 | 3/2002 | Thomas |
| 6,379,660 B1 | 4/2002 | Saavedra et al. |
| 6,432,077 B1 | 8/2002 | Stenzler |
| 6,472,390 B1 | 10/2002 | Stamler et al. |
| 6,494,314 B1 | 12/2002 | Lamborne et al. |
| 6,511,991 B2 | 1/2003 | Hrabie et al. |
| 6,555,058 B2 | 4/2003 | Kamibayashi et al. |
| 6,571,790 B1 | 6/2003 | Weinstein |
| 6,581,599 B1 | 6/2003 | Stenzler |
| 6,601,580 B1 | 8/2003 | Block et al. |
| 6,652,479 B2 * | 11/2003 | Rasor et al. .................. 604/23 |
| 6,673,338 B1 | 1/2004 | Arnold et al. |
| 6,703,046 B2 | 3/2004 | Fitzhugh et al. |
| 6,706,274 B2 | 3/2004 | Herrmann et al. |
| 6,715,485 B1 | 4/2004 | Djupesland |
| 6,747,062 B2 | 6/2004 | Murrell |
| 6,750,254 B2 | 6/2004 | Hrabie et al. |
| 6,758,214 B2 | 7/2004 | Fine et al. |
| 6,780,849 B2 | 8/2004 | Herrmann et al. |
| 6,786,217 B2 | 9/2004 | Stenzler |
| 6,793,644 B2 | 9/2004 | Stenzler |
| 6,796,966 B2 | 9/2004 | Thomas |
| 6,811,965 B2 | 11/2004 | Vodovotz et al. |
| 6,867,194 B2 | 3/2005 | Wang et al. |
| 6,887,485 B2 | 5/2005 | Fitzhugh et al. |
| 6,911,478 B2 | 6/2005 | Hrabie et al. |
| 6,920,876 B2 | 7/2005 | Miller et al. |
| 6,938,357 B2 | 9/2005 | Hauch |
| 6,949,530 B2 | 9/2005 | Hrabie et al. |
| 7,048,951 B1 | 5/2006 | Seitz et al. |
| 7,105,502 B2 | 9/2006 | Arnold et al. |
| 7,118,767 B2 | 10/2006 | Kim et al. |
| 7,122,018 B2 | 10/2006 | Stenzler et al. |
| 7,199,154 B2 | 4/2007 | Berthelette et al. |
| 2002/0069877 A1 | 6/2002 | Villareal |
| 2002/0082566 A1 | 6/2002 | Stenzler |
| 2002/0119115 A1 | 8/2002 | Keefer et al. |
| 2002/0138051 A1 | 9/2002 | Hole et al. |
| 2002/0155164 A1 | 10/2002 | Figley et al. |
| 2002/0156416 A1 | 10/2002 | Stenzler |
| 2002/0169202 A1 | 11/2002 | Sakamoto et al. |
| 2003/0039697 A1 | 2/2003 | Zhao et al. |
| 2003/0150457 A1 | 8/2003 | Miller et al. |
| 2003/0165578 A1 | 9/2003 | Murrell |
| 2003/0203915 A1 | 10/2003 | Fang et al. |
| 2003/0215528 A1 | 11/2003 | Graham et al. |
| 2003/0228564 A1 | 12/2003 | Edrich et al. |
| 2004/0009238 A1 | 1/2004 | Miller et al. |
| 2004/0043026 A1 | 3/2004 | Tuan et al. |
| 2004/0081580 A1 | 4/2004 | Hole et al. |
| 2004/0112378 A1 | 6/2004 | Djupesland |
| 2004/0131703 A1 | 7/2004 | Bach et al. |
| 2004/0163647 A1 | 8/2004 | Figley et al. |
| 2004/0180863 A1 | 9/2004 | Hrabie et al. |
| 2004/0259840 A1 | 12/2004 | Herrmann et al. |
| 2005/0016427 A1 | 1/2005 | Memory |
| 2005/0079148 A1 | 4/2005 | Fitzhugh et al. |
| 2005/0137521 A1 | 6/2005 | Stenzler |
| 2005/0142217 A1 | 6/2005 | Adams et al. |
| 2005/0148566 A1 | 7/2005 | Waterhouse et al. |
| 2005/0171066 A1 | 8/2005 | Shami |
| 2005/0191372 A1 | 9/2005 | Stenzler et al. |
| 2005/0217668 A1 | 10/2005 | Figley et al. |
| 2005/0217679 A1 | 10/2005 | Miller et al. |
| 2005/0251117 A1 | 11/2005 | Anderson et al. |
| 2005/0265958 A1 | 12/2005 | West et al. |
| 2005/0288260 A1 | 12/2005 | Hrabie et al. |
| 2006/0008529 A1 | 1/2006 | Meyerhoff et al. |
| 2006/0068031 A1 | 3/2006 | Miller et al. |
| 2006/0147553 A1 | 7/2006 | Miller et al. |
| 2007/0065473 A1 | 3/2007 | Miller et al. |
| 2007/0086954 A1 | 4/2007 | Miller et al. |
| 2007/0088316 A1 | 4/2007 | Stenzler et al. |
| 2007/0104653 A1 | 5/2007 | Miller et al. |
| 2009/0076475 A1 * | 3/2009 | Ross et al. .................. 604/500 |

FOREIGN PATENT DOCUMENTS

| | | |
|---|---|---|
| EP | 0640357 A1 | 3/1995 |
| EP | 0659445 A1 | 6/1995 |
| EP | 0659445 B1 | 6/1995 |
| EP | 1243278 A2 | 9/2002 |
| FR | 2656218 | 6/1991 |
| JP | 3-139364 | 6/1991 |
| JP | 3-207365 | 9/1991 |
| KR | 202066 | 6/1999 |
| WO | WO 92/17445 | 10/1992 |
| WO | WO 93/15779 | 8/1993 |
| WO | WO 93/17741 | 9/1993 |
| WO | WO 95/09612 | 4/1995 |
| WO | WO 96/00006 | 1/1996 |
| WO | WO 96/22803 | 8/1996 |
| WO | WO 96/25184 | 8/1996 |
| WO | WO 96/31217 | 10/1996 |
| WO | WO 98/01142 | 1/1998 |
| WO | WO 99/49921 | 10/1999 |
| WO | WO 00/07653 | 2/2000 |
| WO | WO 00/30659 | 6/2000 |
| WO | WO 01/65935 A1 | 9/2001 |
| WO | WO 02/056864 A2 | 7/2002 |
| WO | WO 03/066109 A1 | 8/2003 |

| WO | WO 2005/060603 A3 | 7/2005 |
| WO | WO 2005/110052 A3 | 11/2005 |
| WO | WO 2005/110441 A2 | 11/2005 |

OTHER PUBLICATIONS

Ray, James D. et al., "A New Method of Preparing Nitric Oxide," Contribution from the Department of Chemistry, Stanford University (1956).

Shank, J. L. et al., "The Effect of Nitric Oxide on Bacteria," Applied Microbio, No. 10, 189-189 (1962).

Norman, C. et al., "Nitrogen Oxides in Tobacco Smoke," Nature, vol. 205, No. 4971, pp. 915-916, (Feb. 1965).

Canetti, G., "Present aspects of bacterial resistance in tuberculosis," Am. Rev. Respir. Dis. 92:687-703 (1965).

Bass, H. et al., "Regional structure and function in brochiectasis," Am. Rev. Respir. Dis. 97:598-609 (1968).

Contractor, A. M. et al., "Development and Evaluation of an Inhalation Aerosol of Nitroglycerin," Journal of Pharmaceutical Sciences, vol. 63, No. 6, pp. 907-911 (Jun. 1974).

Oda, H. et al., "Nitrosyl-Hemoglobin Formation in the Blood of Animals Exposed to Nitric Oxide," Archives of Environmental Health, vol. 30, No. 7, pp. 453-456 (Sep. 1975).

Katsuki, S. et al., "Stimulation of Guanylate Cyclase by Sodium Nitroprusside, Nitroglycerin and Nitric Oxide in Various Tissue Preparations and Comparison to the Effects of Sodium Azide and Hydroxylamine," Journal of Cyclic Nucleotide Research. vol. 3. pp. 23-25 (1977).

Hugod, C., "Effect of exposure of 43 PPM nitric oxide and 3.6 PPM nitrogen dioxide on rabbit lung," Arch. Occup. Environ. Health 42:159-167 (1979).

Yoshida, J. et al., "Metabolic Fate of Nitric Oxide," Int Arch Occup Environ Health, vol. 46, No. 1, pp. 71-77 (Apr. 1980).

Borland, C., "The Fate of Inhaled Nitric Oxide," Clinical Science, Abstract No. 104, p. 37P (1983).

Mancinelli et al., "Effects of Nitric Oxide and Nitrogen Dioxide on Bacterial Growth," Applied and Environmental Microbiology, vol. 46, No. 1, pp. 198-202 (Jul. 1983).

Demling, R. H. et al., "The Pulmonary and Systemic Response to Recurrent Endotoxemia in the Adult Sheep," Surgery, vol. 100, No. 5, pp. 876-883 (Nov. 1986).

Higenbottam, T., "Primary Pulmonary Hypertension," British Medical Journal, vol. 293, pp. 1456-1457 (Dec. 1986).

Higenbottam, T. et al., "Primary Pulmonary Hypertension," British Medical Journal, vol. 294, p. 705 (Mar. 1987).

Palmer, R.M.J. et al., "Nitric Oxide Release Accounts for the Biological Activity of Endothelium-Derived Relaxing Factor," Nature, vol. 327, pp. 524-526 (Jun. 1987).

Ignarro, L. J. et al., "Endothelium-Derived Relaxing Factor Produced and Released From Artery and Vein is Nitric Oxide," Proceedings of the National Academy of Sciences of the United States of America, vol. 84. No. 24. pp. 9265-9269 (Dec. 1987).

Higenbottam, T. W. et al., "Inhaled 'Endothelium Derived-Relaxing Factor' (EDRF) in Primary Hypertension (PPH)," Abstract, American Review of Respiratory Disease, Suppl., vol. 137. No. 4. Part 2, p. 107 (Apr. 1988).

Ignarro, L. J. et al., "Endothelium-Derived Relaxing Factor and Nitric Oxide Possess Identical Pharmacologic Properties as Relaxants of Bovine Arterial and Venous Smooth Muscle," The Journal of Pharmacology and Experimental Therapeutics, vol. 246. No. 1, pp. 218-226, Jul. 1988.

Dinh-Xuan, A. T. et al., "Non-Prostanoid Endothelium-Derived Vasoactive Factors," The Journal of International Medical Research, vol. 17, pp. 305-315 (1989).

Borland, C. D. R. et al., "A Simultaneous Single Breath Measurement of Pulmonary Diffusing Capacity with Nitric Oxide and Carbon Monoxide," The European Respiratory Journal, vol. 2, No. 1. pp. 56-63 (Jan. 1989).

Buga, G. M. et al., "Endothelium-Derived Nitric Oxide Relaxes Nonvascular Smooth Muscle," European Journal of Pharmacology, vol. 161, No. 1, pp. 61-72, (Feb. 1989).

Garg, U. C. et al., "Nitric Oxide-generating Vasodilators and 8-Bromo-Cyclic Guanosine Monophosphate Inhibit Mitogensis and Proliferation of Cultured Rat Vascular Smooth Muscle Cells," The Journal of Clinical Investigation, vol. 83, No. 5, pp. 1774-1777 (May. 1989).

Meyer, M. et al., "Nitric Oxide (NO), a New Test Gas for Study of Alveolar-capillary Diffusion," The European Respiratory Journal, vol. 2, No. 6, pp. 494-496 (Jun. 1989).

Dinh-Xuan, A. T. et al., "Primary Pulmonary Hypertension: Diagnosis, Medical and Surgical Treatment," vol. 84, pp. 189-197 (1990).

Stavert, D. M. et al., "Nitric Oxide and Nitrogen Dioxide as Inducers of Acute Pulmonary Injury When Inhaled at Relatively High Concentrations for brief Periods," Inhalation Toxicology 2:53-67 (1990).

Moinard, J. et al., "Determination of Lung Capillary Blood Volume and Membrane Diffusing capacity in Patients with COLD using the NO-CO Method," The European Respiratory Journal, vol. 3, pp. 318-322 (1990).

Archer, S. L., "Comparison of the Hemodynamic Effects of Nitric Oxide and Endothelium-Dependent Vasodilators in Intact Lungs," Journal of Applied Physiology, vol. 68, No. 2, pp. 735-747 (Feb. 1990).

Meyer, M. et al., "Pulmonary Diffusing capacities for Nitric Oxide and carbon Monoxide Determined by Rebreathing in Dogs," Journal of Applied Physiology, vol. 68, No. 6, pp. 2344-2357 (Jun. 1990).

Vane, J. R. et al., "Regulatory Functions of the Vascular Endothelium," The New England Journal of Medicine, vol. 323, No. 1, pp. 27-36 (Jul. 1990).

Higenbottam, T. et al., "Has the Treatment of Asthma Improved?" Chest, vol. 98, No. 3, pp. 706-712 (Sep. 1990).

Swami, A. et al., "The Pulmonary Physician and critical Care: 2. The Injury Lung: Conventional and Novel Respiratory Therapy," Thorax, vol. 47, pp. 555-562 (1992).

Bult, H. et al., "Chronic Exposure to Exogenous Nitric Oxide May Suppress its Endogenous Release and Efficacy," Journal of Cardiovascular Pharmacology, vol. 17, Suppl. 3, pp. S79-S82 (1991).

Frostell, C. et al., "Inhaled Nitric Oxide, A Selective Pulmonary Vasodilator Reversing Hypoxic Pulmonary Vasoconstriction," Circulation Journal of the American Heart Association, vol. 83, pp. 2083-2047 (1991).

Hendrickson, D.A. et al, "Regents and Stains," Manual of Clinical Microbiology, 5$^{th}$ Ed., American Society for Microbiology, pp. 1289-1314 (1991).

Cremona, g. et al., "Endothelium-derived Relaxing Factor and the Pulmonary Circulation," Lung, vol. 169, pp. 185-202 (1991).

Falke, K. et al., "Inhaled Nitric Oxide Selectively Reduces Pulmonary Hypertension in Severe ARDS and Improves Gas Exchange as well as right Heart Ejection fraction—A Case Report." Abstract 248, Am. Rev. Respir. Dis., vol. 143 (1991).

Fratacci, M. D., "Inhaled Nitric Oxide—A Selective Pulmonary Vasodilator of Heparin-Protamine Vasoconstriction in Sheep," Anesthesiology, vol. 75, pp. 990-999 (1991).

Denis, M., "Interferon—Gamma-treated Murine Macrophages Inhibit Growth of *Tubercle bacilli* via the Generation of Reactive Nitrogen Intermediates," Cellular Immunology, vol. 132, No. 1. pp. 150-157 (Jan. 1991).

Dinh-Xuan, A. T. et al., "Impairment of Endothelium-Dependent Pulmonary-Artery Relaxation in Chronic Obstructive Lung Disease," The New England Journal of Medicine, vol. 324. No. 22. pp. 1539-1547 (May 1991).

Frostell, C. et al., "Inhaled Nitric Oxide—A Selective Pulmonary Vasodilator Reversing Hypoxic Pulmonary Vasoconstriction," Circulation, vol. 83, No. 6 (Jun. 1991).

Moncada, S. et al., "Nitric Oxide: Physiology, Pathophysiology, and Pharmacology," Pharmacological Reviews, vol. 43, No. 2 (Jun. 1991).

Frostell, C. et al., "Inhaled Nitric Oxide Dilates Human Hypoxic Pulmonary Vasoconstriction Without Causing Systemic Vasodilation," Anesthesiology, The Journal of the American Society of Anesthesiologists, Inc., vol. 75, No. 3A. Abstract A989 (Sep. 1991).

Girard, C. et al., "Inhaled Nitric Oxide (NO) in Pulmonary Hypertension Following Mitral Valve Replacement," Anesthesiology, The Journal of the American Society of Anesthesiologists. Inc. vol., 75. No. 3A, Abstract A983 (Sep. 1991).

Roberts, J. D. et al., "Inhaled Nitric Oxide (NO): A Selective Pulmonary Vasodilator for the Treatment of Persistent Pulmonary Hypertension of the Newborn (PPHN)," Abstract 1279, Circulation. vol. 84. No. 4. p. II-321 (Oct. 1991).

Pepke-Zaba, J. et al., "Inhaled Nitric Oxide as a Cause of Selective Pulmonary Vasodilatation in Pulmonary Hypertension," The Lancet, vol. 338, No. 8776, pp. 1173-1174 (Nov. 1991).

Radomski, M. W., et al., "Human Colorectal Adenocarcinoma Cells: Differential Nitric Oxide Synthesis Determines Their Ability to Aggregate Platelets," Cancer Research, vol. 51, pp. 6073-6078 (Nov. 15, 1991).

Johns, R. A., "EDRF/Nitric Oxide—The Endogenous Nitrovasodilator and a New cellular Messenger," Anesthesiology, The Journal of The American Society of Anesthesiologists, Inc., vol. 75. No. 6. pp. 927-931 (Dec. 1991).

Pearl, R. G., "The Pulmonary Circulation," Anesthesiology, vol. 5, pp. 848-854 (1992).

Chan, J. et al., "Killing of Virulent Mycobacterium Tuberculosis by Reactive Nitrogen Intermediates Produced by Activated Murine Macophages," J. Exp. Med. 175:1111-1122 (Apr. 1992).

Rossiant, R. et al., "Successful Treatment of Severe Adult Respiratory Distress Syndrome with Inhaled Nitric Oxide," American Review of Respiratory Disease, Suppl., vol. 145, No. 4. Part 2. p. A80 (Apr. 1992).

Rossiant, R. et al., "Inhaled Nitric Oxide in Contrast to Infused Prostacyclin Selectively Reduces Pulmonary Hypertension and Improves Gas Exchange in Severe ARDS," Abstract. American Review of Respiratory Disease. Suppl., vol. 145 No. 4, Part 2. p. A185, Apr. 1992.

Bigatello, L. M., "Inhaled Nitric Oxide is a Selective Pulmonary Vasodilator in Septic Patients with Severe ARDS," Abstract, American Review of Respiratory Disease, Suppl., vol. 145. No. 4, Part 2, p. A185 (Apr. 1992).

Snyder, S. H. et al., Biological Roles of Nitric Oxide, Scientific American, vol. 266, No. 5, pp. 68-77 (May 1992).

Foubert, L., "Safety Guidelines for Use of Nitric Oxide," The Lancet, vol. 339, No. 8809, pp. 1615-1616 (Jun. 1992).

Messent, M. et al., "Pharmacotherapy in Lung Injury," Thorax, vol. 47, No. 7, pp. 651-656 (Jul. 1992).

Barash, P. et al., "Anesthesiology," The Journal of the American Medical Association, vol. 268, No. 3, pp. 335-337 (Jul. 1992).

Dupuy, P. M. et al., "Bronchodilator Action of Inhaled Nitric Oxide in Guinea Pigs," J. Clin. Invest., vol. 90, pp. 421-428 (Aug. 1992).

Kinsella, J. P. et al., "Hemodynamic Effects of Exogenous Nitric Oxide in Ovine Transitional Pulmonary Circulation," American Journal of Physiology: Heart and Circulatory Physiology, vol. 32, No. 3, pp. H875-H880 (Sep. 1992).

Roberts, J. D. et al., "Inhaled Nitric Oxide in Persistent Pulmonary Hypertension of the Newborn," The Lancet, vol. 340, pp. 818-819 (Oct. 1992).

Kinsella, J. P. et al., "Low-Dose Inhalational Nitric Oxide in Persistent Pulmonary Hypertension of the Newborn," The Lancet, vol. 340, pp. 819-820 (Oct. 1992).

Girard, C. et al., "Inhaled Nitric Oxide After Mitral Valve Replacement in Patients with Chronic Pulmonary Artery Hypertension," Anesthesiology, The Journal of the American Society of Anesthesiologists. Inc., vol. 77, No. 5. pp. 880-883 (Nov. 1992).

Kacmarek, R. M., "Nitric Oxide as a Bronchodilator in Methacholine Induced Bronchospasm in Mild Asthmatics," Abstract (1993).

Blomqvist, H. et al., "Enhanced Pneumonia Resolution by Inhalation of Nitric Oxide?" Acta Anaesthesiol Scand, vol. 37, pp. 110-114 (1993).

Buga, G. M. et al., "Negative Feedback Regulation of Endothelial Cell Function by Nitric Oxide," Circulation Research, Journal of the American Heart Association, 73:808-812 (1993).

Higenbottam, T., "Inhaled Nitric Oxide: A Magic Bullet?" Quarterly Journal of Medicine, vol. 86, pp. 555-558 (1993).

Stenqvist, O. et al., "Evaluation of a New System for Ventilatory Administration of Nitric Oxide," Acta Anaesthesiologica Scandinavica, pp. 687-691 (1993).

Rossaint, R. et al., "Inhaled Nitric Oxide For The Adult Respiratory Distress Syndrome," New England Journal of Medicine, vol. 328, pp. 399-405 (Feb. 1993).

Maragos, C. M., et al., "Nitric Oxide/Nucleophile Complexes Inhibit the in Vitro Proliferation of A375 Melanoma Cells via Nitric Oxide Release," Cancer Research, vol. 53, pp. 564-568 (Feb. 1, 1993).

Pearl, R. G., "Inhaled Nitric Oxide—The Past, The Present and the Future," Anesthesiology, vol. 78, No. 3, pp. 413-416 (Mar. 1993).

Assreuy, J. et al., "Feedback Inhibition of Nitric Oxide Synthase Activity by Nitric Oxide," British Journal of Pharmacology, vol. 108, pp. 883-837 (Mar. 1993).

Higenbottam, T. et al., "Highlights on Pulmonary Hypertension: A Commentary," The European Respiratory Journal, vol. 6, No. 7, pp. 932-933 (Jul. 1993).

Haworth, S. G., "Pulmonary Hypertension in Childhood," The European Respiratory Journal, vol. 6, No. 7, pp. 1037-1043 (Jul. 1993).

Higenbottam, T. et al., "Acute and Chronic Hypoxic Pulmonary Hypertension," The European Respiratory Journal, vol. 6, No. 8, pp. 1207-1212 (Sep. 1993).

Mansch, R. et al., "Simulation of Microbiologically and chemically Influenced corrosion of Natural Sandstone," Abstract, ASTM Special Technical Publication, 203-16; 1 pg. (1994).

Lowenstein, C. J. et al., "Nitric Oxide: a Physiologic Messenger," Annals of Internal Medicine, vol. 120, Issue 3, pp. 227-237 (Feb. 1994).

Dong, Z., et al., "Inverse Correlation Between Expression of Inducible Nitric Oxide Synthase Activity and Production of Metastasis in K-1735 Murine Melanoma Cells," Cancer Research, vol. 54. pp. 789-793 (Feb. 1, 1994).

Butt, A. Y. et al, "New Therapies for Primary Pulmonary Hypertension," Chest, vol. 105, No. 2, pp. 21S-25S (Feb. 1994).

Foubert, L. et al., "Nitric Oxide in Pulmonary Hypertension: Therapeutic Considerations," Journal of Cardiothoracic and Vascular Anesthesia, vol. 8, No. 3, Suppl. 2, p. 41 (Jun. 1994).

Snow, D. et al., "Inhaled Nitric Oxide in Pulmonary Hypertension," Journal of Cardiothoracic and Vascular Anesthesia, vol. 8, No. 3, Suppl. 2, Abstract No. 127 (Jun. 1994).

O'Brien, L. et al., Strains of *Mycobacterium tuberculosis* Differ in Susceptibility to Reactive Nitrogen Intermediates in Vitro, Infection and Immunity, vol. 62, No. 11, pp. 5187-5190 (Aug. 1994).

Young, J. D., "A Universal Nitric Oxide Delivery System," British Journal of Anaesthesia, vol. 73, No. 4, pp. 700-702 (Oct. 1994).

Hanson, S. R., et al., "Nitric Oxide Donors: A Continuing Opportunity in Drug Design," Nitric Oxide Biochemistry, Molecular Biology, and Therapeutic Implications, Advances in Pharmacology, vol. 34, pp. 383-398 (1995).

Chan, J. et al., "Effects of Nitric Oxide Synthase Inhibitors on Murine Infection with *Mycobacterium tuberculosis*," Infection and Immunity, vol. 63, No. 2., pp. 736-740 (Feb. 1995).

DeGroote, M. A., et al., "NO Inhibitions: Antimicrobial Properties of Nitric Oxide," Clinical Infectious Diseases, vol. 21, Suppl. 2, pp. S162-S165 (Oct. 1995).

Body, S. C., M.D. et al., "Nitric Oxide: Delivery, Measurement, and Clinical Application," Journal of Cardiothoracic and Vascular Anesthesia, vol. 9, No. 6; pp. 748-763 (Dec. 1995).

Higenbottam, T. et al., "The Treatment of Primary Pulmonary Hypertension," Therapeutic Applications of Iloprost, A Volume in the Clinical Monograph Series, pp. 35-41 (Apr. 1995).

Szabo, C., "The Pathophysiological Role of Peroxynitrite in Shock, Inflammation and Ischemia-Reperfusion Injury," Shock, vol. 6, No. 2, pp. 79-88 (1996).

Higenbottam, T., "Nitric Oxide and the Lung," Horizons in Medicine, No. 7 pp. 203-224.

Young, J. D. et al., "Delivery and Monitoring of Inhaled Nitric. Oxide," Intensive Care Medicine, vol. 22, No. 1, pp. 77-86 (Jan. 1996).

Mellgren, K., et al., "Nitric Oxide in the Oxygenator Sweep Gas Reduces Platelet Activation During Experimental Perfusion," The Annals of Thoracic Surgery, vol. 61, No. 4, pp. 1194-1198 (Apr. 1996).

Ramnarine, S. I., et al., "Nitric Oxide Inhibition of Basal and Neurogenic Mucus Secretion in Feerrete Trachea in Vitro," British Journal of Pharmacology, vol. 118 (4), pp. 998-1002 (Jun. 1996).

Channick, R. N., M.D. et al., "Pulsed Delivery of Inhaled Nitric Oxide to Patients with Primary Pulmonary Hypertension," Chest, The Cardiopulmonary and Critical Care Journal, vol. 109. No. 6. pp. 1545-1549 (Jun. 1996).

Hudome, S. M., M.D. et al., "Precise Control of Nitric Oxide Concentration in the Inspired Gas of Continuous Flow Respiratory Devices," Pediatric Pulmonology, vol. 22, No. 3, pp. 182-187 (Sep. 1996).

Cuthbertson, B. H. et al., "Inhaled Nitric Oxide," The Lancet, vol. 348, No. 9039, pp. 1447-1448 (Nov. 1996).

Gerlach, H. et al., "Low Levels of Inhaled Nitric Oxide in Acute Lung Injury," Nitric Oxide and the Lung, vol. 98, Chapter 14, pp. 271-283 (1997).

Dupuy, P. M. et al., "Bronchial Effects of Nitric Oxide," Nitric Oxide and the Lung, vol. 98, Chapter 15, pp. 285-311 (1997).

Leopold, J. A. et al., "New Developments in Nitrosovasodilator Therapy," Vascular Medicine, vol. 2, No. 3 (1997).

Rook, G. A. W., "Intractable Mycobacterial Infections Associated with Genetic Defects in the Receptor for Interferon Gamma: What Does This Tell Us About immunity to Mycobacteria?" Thorax, vol. 52 (Suppl. 3), pp. S41-S46 (1997).

Katayama, Y. et al., "Inhaled Nitric Oxide and Arterial Oxygen Tension in Patients with chronic Obstructive Pulmonary Disease and Severe Pulmonary Hypertension," Thorax, The Journal of the British Thoracic Society, vol. 52, pp. 120-124 (1997).

Neonatal Inhaled Nitric Oxide Study Group, "Inhaled Nitric Oxide in Full-Term and Nearly Full-Term Infants with Hypoxic Respiratory Failure," New England Journal of Medicine, 336(9):597-604 (Feb. 1997).

Roberts, J. D. et al., "Inhaled Nitric Oxide and Persistent Pulmonary Hypertension of the Newborn," New England Journal of Medicine, 336:605-610 (Feb. 1997).

Imanaka, H., M.D. et al., "Inaccuracies of Nitric Oxide Delivery Systems During Adult Mechanical Ventilation," Anesthesiology, vol. 86, No. 3, pp. 676-688 (Mar. 1997).

Marriott, H. et al., "The Role of Nitric Oxide in Respiratory Disease," Schweiz Med Wochenschr, vol. 127, pp. 709-714 (Apr. 1997).

Nozaki, Y. et al., "Mechanism of Nitric Oxide-Dependent Killing of *Mycobacterium bovis* BCG in Human Alveolar Macrophages," Infection and Immunity, vol. 65, pp. 3644-3647 (Sep. 1997).

Hess, D., RRT, Ph.D. et al., "Delivery Systems for Inhaled Nitric Oxide," Respiratory Care Clinics of North America, vol. 3, No. 3, pp. 371-410 (Sep. 1997).

Hoehn T., M.D. et al., "Effect of Therapeutic Concentrations of Nitric Oxide on Bacterial Grown in Vitro," Crit Care Med, vol. 26, No. 11, pp. 1857-1862 (1998).

Bauer, J. A. et al., Evaluation of Linear Polyethylenei-mine/Nitric Oxide Adduct on Wound Repair: Therapy Versus Toxicity, The Wound Healing Society, pp. 569-577 (1998).

Pizzichini, M. M. M. et al., "Asthma and Natural Colds: Inflammatory Indices in Induced Sputum: A Feasibility Study," American Journal of Respiratory Critical Care Medicine, vol. 158, pp. 1178-1184 (1998).

Higenbottam, T. et al., "Primary and Secondary Pulmonary Hypertension," Seminars in Respiratory and Critical Care Medicine, vol. 19, No. 1, pp. 91-95 (1998).

Long R. et al., "Pulmonary Tuberculosis Treated with Directly Observed Therapy: Serial Changes in Lung Structure and Function," Chest, vol. 113, pp. 933-943 (1998).

Klein, M.D. et al., "Nitric Oxide Delivery Systems," Acta Anaesthesiologica Scandinavica, pp. 274-275 (1998).

Francoe, M, RRT et al., "Inhaled Nitric Oxide: Technical Aspects of Administration and Monitoring," Critical Care Medicine, vol. 26, No. 4, pp. 782-796 (Apr. 1998).

Keefer, L. K., "Nitric Oxide-Releasing Compounds: From Basic Research to Promising Drugs," The American Chemical Society, vol. 28, pp. 30-35 (Aug. 1998).

Ivy, D. D., M.D. et al., "Acute Hemodynamic Effects of Pulsed Delivery of Low Flow Nasal Nitric Oxide in Children with Pulmonary Hypertension," The Journal of Pediatrics, vol. 133, No. 3, pp. 453-456 (Sep. 1998).

Hiesmayr, M. J. et al., "Performance of Proportional and Continuous Nitric Oxide Delivery Systems During Pressure and Volume-Controlled Ventilation," The British Journal of Anaesthesia, vol. 81, No. 4, pp. 544-552 (Oct. 1998).

Katayama, Y., M.D. et al., "Minimizing the Inhaled Dose of NO With Breath-by-Breath Delivery of Spikes of Concentrated Gas," Circulation, Journal of the American Heart Association, vol. 98, No. 22 (Dec. 1998).

Higenbottam, T. et al., "Treatments for Severe Pulmonary Hypertension," The Lancet, vol. 353, No. 9150, pp. 338-340 (Jan. 1999).

Long, R. et al., "Mycobacteriocidal Action of Exogenous Nitric Oxide," Antimicrobial Agents and Chemotherapy, vol. 43, No. 2, pp. 403-405, (Feb. 1999).

Schofnagl, H. et al., "Proportional and Continuous NO Delivery Systems," British Journal of Anaesthesia, vol. 82, No. 4, pp. 647-653 (Apr. 1999).

Rimmelzwaan, G. F. et al., "Inhibition of Influenza Virus Replication by Nitric Oxide," Journal of Virology, American Society for Microbiology, vol. 73, No. 10, pp. 8880-8883 (Oct. 1999).

Webert, K.E., M.D. et al., "Effects of Inhaled Nitric Oxide In A Rat Model of *Pseudomonas ceruginosa* Pneumonia," Crit Car Med, vol. 28, No. 7, pp. 2397-2405 (2000).

Tamaoki, J., M.D., et al., "Impairment of Airway Mucociliary Transport in Patients with Sinobrochial Syndrome: Role of Nitric Oxide," Journal of Aerosol Medicine, vol. 13, No. 3, pp. 239-244 (Nov. 2000).

Long et al., "Treatment of Sputum-Smear Positive Pulmonary Tuberculosis With Inhaled Nitric Oxide," 2001—Abstract Form to the ATS 2001 San Francisco, May 18-23, 2001 (faxed Mar. 27, 2001).

Frank, S., et al., "Nitric Oxide Drives Skin Repair: Novel Functions Of An Established Mediator," Kidney International, vol. 61, pp. 882-888 (2002).

Imada, M., et al., "Functional Roles of Nasal Nitric Oxide in Nasal Patency and Mucociliary Function," ACTA Oto-Laryngologica, vol. 122, No. 5, pp. 513-519 (Jul. 2002).

Kirov, M. Y., M.D., et al., "Combination of Intravenously Infused Methylene Blue and Inhaled Nitric Oxide Ameliorates Endotoxin-Induced Lung Injury in Awake Sheep," Critical Care Medicine, vol. 31, No. 1, pp. 179-186 (Jan. 2003).

Shami, P. J., et al., JS-K, A Glutathione/Glutathione S-Transferase-activated Nitric Oxide Donor of the Diazeniumdiolate Class with Potent Antineoplastic Activity, Molecular Cancer Therapeutics. vol. 2. pp. 409-417 (Apr. 2003).

Counter-Defendant's First Amended Responses to Counterclaimant's Second Set of Interrogatories Relating to Counterclaims (Nos. 19-38) (Oct. 2003).

Miller, Chris C. et al.; "Treatment of Chronic Nonhealing Leg Ulceration with Gaseous Nitric Oxide: A Case Study"; Journal of Cutaneous Medicine and Surgery, pp. 233-238 (2004).

Vijh, A. K., "High Infectious Burden, Low Cancer Incidence, and Early Malignancy in Developing Countries: A Molecular Hypothesis in Term of the Role of Nitric Oxide," Medical Hypotheses: vol. 63. pp. 208-210 (Feb. 2004).

Sanders, S. P. et al., "Role of Nasal Nitric Oxide in the Resolution of Experimental Rhinovirus Infection," Journal of Allergy and Clinical Immunology, vol. 113, No. 4, pp. 697-702 (Apr. 2004).

Schmidt, I. et al., Physiologic and Proteomic Evidence for a Role of Nitric Oxide in Biofilm Formation by *Nitrosomonas europaea* and Other Ammonia Oxidizers; Journal of Bacteriology, vol. 186. No. 9. pp. 2781-2788 (May 2004).

Reynolds, M. M., et al., "Nitric Oxide-Releasing Hydrophobic Polymers: Preparation, Characterization, and Potential Biomedical Applications," Free Radical Biology & Medicine, The Official Journal for the Society for Free Radical Biology and Medicine, vol. 37, No. 7, pp. 926-936 (Oct. 2004).

Lechner, M., et al., "Inducible Nitric Oxide Synthase (iNOS) in Tumor Biology: The Two Sides of the Same Coin," Seminars in Cancer Biology, vol. 15, pp. 277-289 (2005).

Ghaffair, A., et al., "A Direct Nitric Oxide Gas Delivery System for Bacterial and Mammalian Cell Cultures," Nitric Oxide Biology and Chemistry, vol. 12, pp. 129-140 (2005).

Proud, D., "Nitric Oxide and the Common Cold," Journal of Allergy and Clinical Immunology, vol. 5, pp. 37-42 (2005).

Nablo, B. J., et al., Inhibition of Implant-Associated Infections Via Nitric Oxide Release, Science Direct, Biomaterials, vol. 26, pp. 6984-6990 (May 2005).

McMullin, B. B., MSc RRT, et al., "The Antimicrobial Effect of Nitric Oxide on the Bacteria That Cause Nosocomial Pneumonia in Mechanically Ventilated Patients in the Intensive Care Unit," Respiratory Care, vol. 50, No. 11. pp. 1451-1456 (Nov. 2005).

Hurford, W. E.; Nitric Oxide As A Bacterial Agent: Is The Cure Worse Than The Disease?; Respiratory Care, vol. 50, No. 11, pp. 1428-1429 (Nov. 2005).

Turchi, J. J., "Nitric Oxide and Cisplatin Resistance: NO Easy Answers," PNAS, vol. 103, No. 12, pp. 4337-4338 (Mar. 21, 2006).

Hagenah, Jens-Uwe, "The Use of Nitric Oxide (NO) in Intensive Care Ventilation," Dragerwerk Aktiengesellscha, pp. 1 and 3-36 (Apr. 25, 1995).

Katayama, Y. et al., "A Minimal Dose of Inhaled Nitric Oxide Delivered As A 'Spike' of Small Volume In Early Inhalation," Section of Respiratory Medicine, Division of Clinical Sciences, The Medical School, University of Sheffield (23 pages) (as early as Apr. 27, 1998).

* cited by examiner

FIG. 6
FIG. 6A
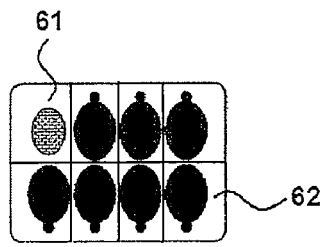
FIG. 6E
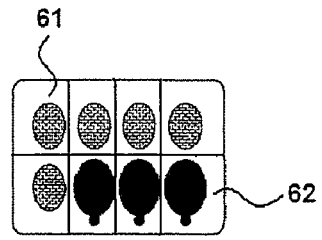
FIG. 6B
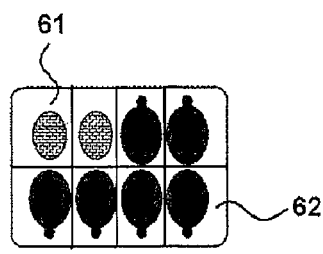
FIG. 6F
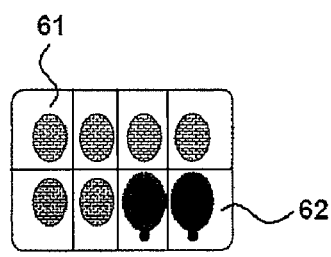
FIG. 6C
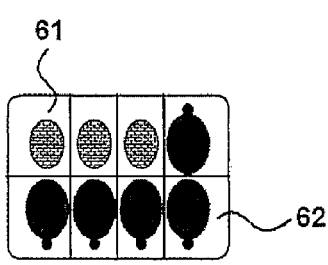
FIG. 6G
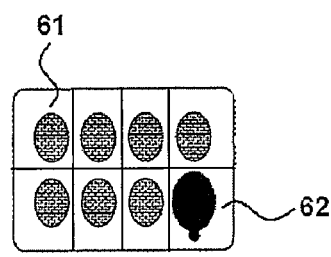
FIG. 6D
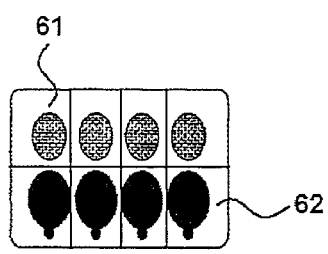
FIG. 6H
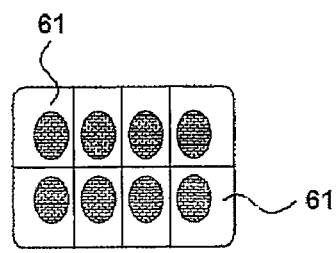

Cell Opening Sequence

FIG. 10
FIG. 10A
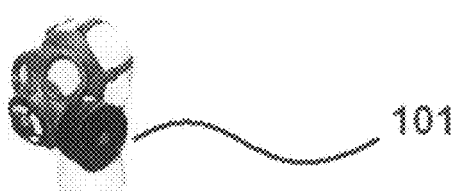 — 101
FIG. 10B
 — 102
FIG. 10C
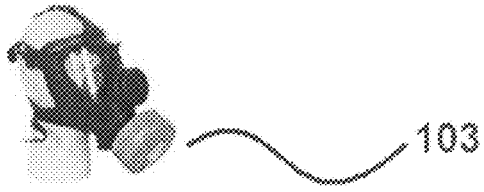 — 103
FIG. 10D
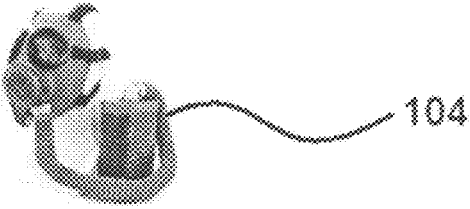 — 104
FIG. 11A
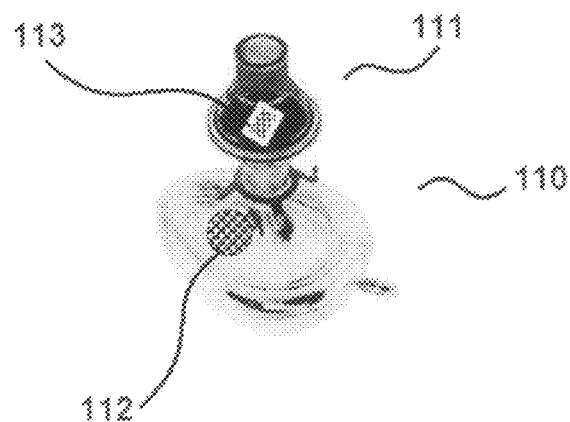
113   111
      110
112

METHODS AND DEVICES FOR THE DELIVERY OF THERAPEUTIC GASES INCLUDING NITRIC OXIDE

CLAIM OF PRIORITY

This application claims priority to U.S. Provisional Patent Application Ser. No. 60/853,103, filed on Oct. 20, 2006, which is expressly incorporated herein by reference in its entirety.

FIELD OF THE INVENTION

The invention generally relates to methods and devices for the delivery of therapeutic gases. The therapeutic gases, for example, may be delivered to situs on or in animal and human bodies and elsewhere. More particularly, the invention relates to methods and devices for delivering gaseous nitric oxide (gNO) to situs on or in animal and human bodies. The methods and devices may be useful to treat a variety of medical and non-medical conditions and impart other desirable effects, such as sterilization, that are caused by the delivery of gNO or other gases to animal and human tissues.

BACKGROUND OF THE INVENTION

Therapeutic gases may be applied to the body for the purpose of treating a variety of medical and non-medical conditions and producing other desirable effects. For example, gaseous nitric oxide (gNO) has been studied for its effects on infectious microorganisms, vasodilatation, skin diseases, respiratory infections, inflammation, bronchoconstriction, and the like. The biochemical mechanisms of action for gNO continue to be investigated.

In recent years, research has been directed to creating devices capable of delivering gNO from pressurized cylinders through distribution piping and delivery apparatuses in order to administer gNO at controlled doses to different tissue sites on or in the body. This approach is complicated by the relatively sophisticated electromechanical devices that are required to accurately and safely deliver the gNO. For example, the use of high pressure cylinders carries penalties of weight and size and requires the safe regulation of pressure down to pressures low enough to be suitable for application to tissues. Another limitation is that gas cylinders have elaborate distribution, management, recovery, and disposal needs, especially larger cylinders and cylinders that are intended to last for more than one therapy session. The complexity of this approach, therefore, can be costly.

Research and development also recently has been directed towards developing polymers with the capability of generating and releasing gNO. For example, some polymers can be stimulated to undergo an internal chemical reaction or conversion that releases gNO directly from the polymer. Typically, this internal chemical reaction or conversion occurs when the polymer is placed in contact with moisture. This approach may be limited by the complexity and cost of manufacturing such polymers.

Some polymers have the ability to absorb a therapeutic gas if they are placed in a gas rich environment and then release the gas at a later time if the surrounding level of the gas drops, consistent with the principles of diffusion. This method requires that the polymer be charged with the therapeutic gas before use and then applied to the desired delivery site. This approach may be limited by the polymer's potential to absorb the therapeutic gas, the requirement that the operator charge the polymer before use, and the dependence of the subsequent delivery on the surrounding gas concentration, temperature, and other environmental variables.

The description herein of problems and disadvantages of known apparatus, methods, and devices is not intended to limit the invention to the exclusion of these known entities. Indeed, embodiments of the invention may include one or more of the known apparatus, methods, and devices without suffering from the disadvantages and problems noted herein.

SUMMARY OF THE INVENTION

There is a need for more improved methods and devices for the delivery of therapeutic gases, and especially gaseous nitric oxide (gNO), to situs on or in animal and human bodies. There also is a need for methods and devices for the delivery of therapeutic gases, and especially gNO, that are simpler, less cumbersome, lighter, and more cost effective than utilizing pressurized gas cylinders, delivery piping, and end delivery apparatus. Furthermore, there is a need for methods and devices for the delivery of therapeutic gases, especially gNO, that are less complex, less cumbersome, lighter, and more cost effective than utilizing gas generators configured in a similar manner to the gas cylinder delivery approach discussed above. There is a further need for methods and devices for delivering sterilizing gaseous agents in order to sterilize medical devices, enclosures such as rooms, medical equipment, and so forth.

Accordingly, there is provided herein devices for the delivery of therapeutic gases, and especially gNO.

An exemplary device for supplying one or more therapeutic gases is a gas package comprising: a reservoir that is capable of supplying the therapeutic gases; an interface layer that regulates the flow of the therapeutic gases from the reservoir to an environment external to the device; and an element that prevents the flow of therapeutic gases to the external environment until the device is activated, and that is selected from the group consisting of a sealing layer and a holding container.

Another exemplary device for supplying one or more therapeutic gases is a gas patch comprising: a reservoir that is capable of supplying the therapeutic gases; and an interface layer that regulates the flow of the therapeutic gases from the reservoir to an environment external to the patch; wherein the interface layer is provided with structural tension members that are capable of maintaining the shape and geometry of the gas patch.

Still another exemplary device for supplying one or more therapeutic gases is a tension-type bandage for placement over a wound, comprising: a reservoir that is capable of supplying the therapeutic gases; an interface layer that regulates the flow of the therapeutic gases from the reservoir to the wound; and an element that prevents the flow of therapeutic gases through the interface layer to the wound until the device is activated, and that is selected from the group consisting of a sealing layer and a holding container. The reservoir, interface layer, sealing layer, and holding container are incorporated into the body of a tension-type bandage.

There also is provided methods for administering therapeutic gases, and especially gNO.

An exemplary method of administering one or more therapeutic gases to an animal or human patient comprises providing a reservoir that is capable of supplying the therapeutic gases and an interface layer through which the gases must transit in order to reach the patient; providing an element that prevents the flow of therapeutic gases through the interface layer to the patient until the device is activated, and that is selected from the group consisting of a sealing layer and a holding container; compromising the sealing layer or holding container; and allowing the therapeutic gases to transit from the reservoir through the interface layer to the patient.

There also is provided methods of creating or maintaining a sterile field or volume using sterilizing gases. An exemplary method comprises: providing a reservoir that is capable of supplying the therapeutic gases and an interface layer through which the gases must transit in order to reach the field or volume; providing an element that prevents the flow of therapeutic gases through the interface layer to the field or volume until the device is activated, and that is selected from the group consisting of a sealing layer and a holding container; compromising the sealing layer or holding container; and allowing the therapeutic gases to transit from the reservoir through the interface layer to the field or volume.

There also is provided methods of administering one or more therapeutic gases to a flowing fluid. An exemplary method comprises providing a flow-through element; providing in the flow-through element a reservoir that is capable of supplying the therapeutic gases and an interface layer through which the gases must transit in order to reach the flowing fluid; passing a fluid through the flow-through element; and allowing the gases to transit from the reservoir through the interface layer and enter the flowing fluid.

There also is provided methods of treating and/or preventing disease and non-disease states in an animal or human patient. An exemplary method comprises administering one or more therapeutic gases to the patient from one or more gas package devices, wherein the gas package devices comprise a reservoir that is capable of supplying the therapeutic gases; an interface layer that regulates the flow of the therapeutic gases from the reservoir to the patient; and an element that prevents the flow of therapeutic gases through the interface layer to the patient until the device is activated, and that is selected from the group consisting of a sealing layer and a holding container.

These and other devices, methods, features, and advantages will be apparent from the description provide herein.

BRIEF DESCRIPTION OF THE DRAWINGS

The nature and scope of the invention will be elaborated in the detailed description which follows, in connection with the figures.

FIG. 6, embodiments A-H, illustrates an exemplary multi-reservoir gas package.

FIG. 10, embodiments A-D, illustrates gas packages that may be used in place of existing gas conditioning cartridges.

DETAILED DESCRIPTION OF THE INVENTIONS

Figure 1A:
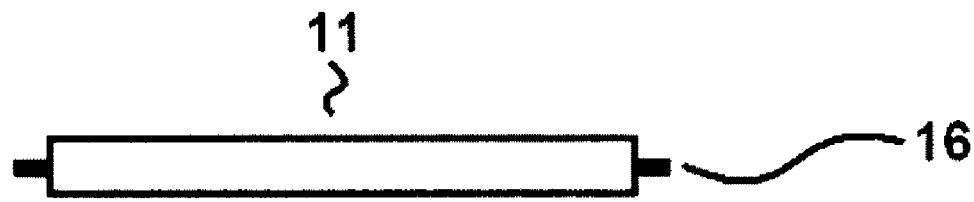
FIG. 1, embodiments A-G, illustrates an exemplary gas package and associated gas patch.
Figure 1B:
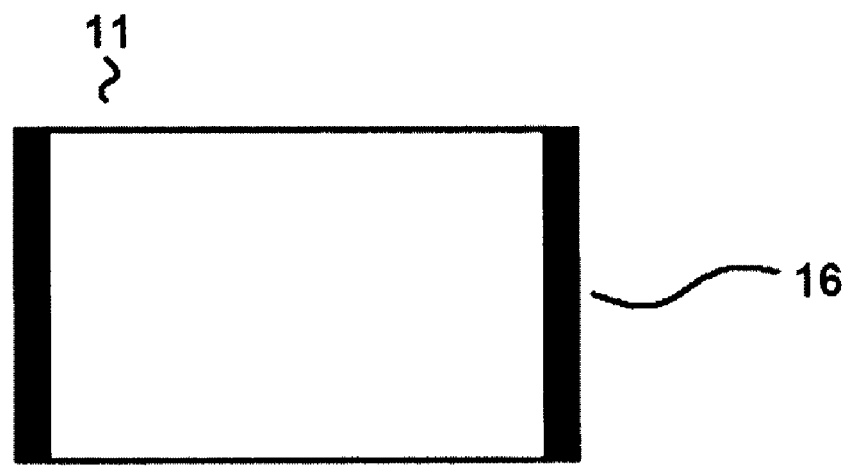
Figure 1C:
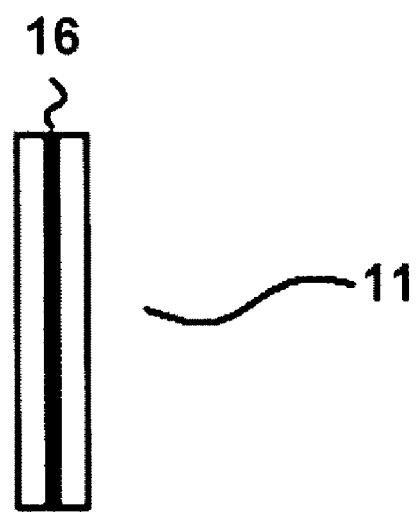
Figure 1D:
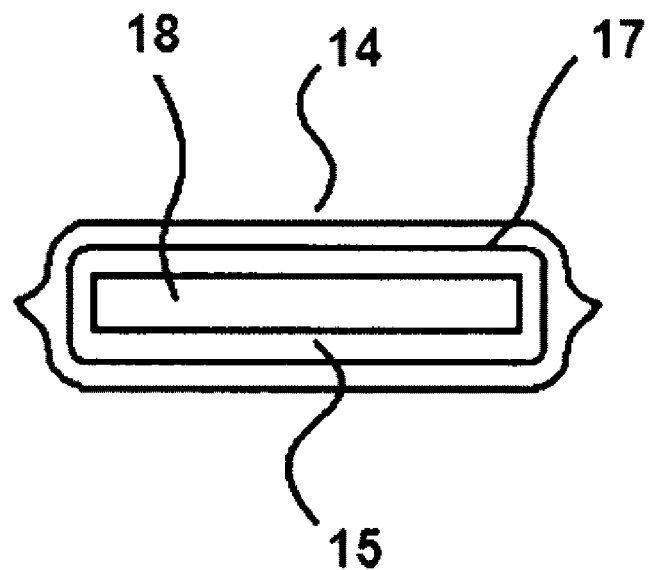

As used throughout this disclosure, the singular forms "a," "an," and "the" include plural reference unless the context clearly dictates otherwise.

All technical and scientific terms used herein have the same meanings as commonly understood by one of ordinary skill in the art to which this invention belongs, excepting terms, phrases, and other language defined herein. All publications mentioned herein are cited for the purpose of describing and disclosing the embodiments. Nothing herein is to be construed as an admission that the embodiments described are not entitled to antedate such disclosures by virtue of prior invention.

Before the present compositions and methods are described, it is to be understood that this invention is not limited to the particular devices, compositions, methodologies or protocols described, as these may vary. It is also to be understood that the terminology used in the description is for the purpose of describing the particular versions or embodiments only, and is not intended to limit the scope of the present invention which will be limited only by the appended claims. For simplicity, each reference referred to herein shall be deemed expressly incorporated by reference in its entirety as if fully set forth herein.

Described herein are devices and methods for the delivery of therapeutic gases, and especially gNO. The therapeutic gases may be delivered, for example, to situs in or on animal and human bodies. The gas delivery devices are in the form of "gas packages," "gas patches," and other devices. The devices described herein may mitigate, alleviate, and even eliminate some of the identified deficiencies or disadvantages in the current art of delivering therapeutic gases. The devices provide the ability to deliver therapeutic gases to a wide variety of surfaces, volumes, and locations. The devices also provide the ability to deliver therapeutic gases at a predictable, configurable, and adjustable rate. The devices also may be used singularly or in plurality in order to achieve a wide variety of customizable therapeutic gas delivery profiles.

The ability of therapeutic gases to affect disease and non-disease, medical and non-medical conditions in the body and elsewhere may depend on the delivery profile of the therapeutic gases. The devices described herein may be capable of delivering therapeutic gases in a wide range of mass flow rates over a wide range of time periods. The devices described herein also may provide improved economics and increased simplicity while simultaneously retaining the capability of delivering therapeutic gases under a wide range of prescribed profiles. The devices described herein may provide further benefits as they can be manufactured to be easily disposable, and preferably capable of being recycled.

As used herein, "gas package" is any combination of one or more of a reservoir, interface layer, sealing layer, and a holding container that may work in combination to control the flow of delivery gas before and/or during delivery.

As used herein, "reservoir" is any physical volume defined or restricted by a physical barrier. The reservoir may be intended to act in combination with one or more interface layers and/or sealing layers to produce a desired flow of delivered gas. The physical barrier defining the reservoir preferably is an interface layer or a sealing layer.

As used herein, "interface layer" is a physical barrier that slows, impedes, or controls the amount and rate of flow of gas molecules from one side of the interface layer (e.g., the internal side) to the other of the interface layer (e.g., the external side). The interface layer may be made of a gas permeable material that defines and surrounds the reservoir.

This interface layer may be, for example: a polymeric material; a thin membrane; a planar structure formed from an array of small openings that act as a microscopic orifices, such as nano-structures designed to act as orifices; a densely woven or non-woven fabric, screen, or mesh; a porous solid such as a porous ceramic; a material layer with stitched seams; and any other material configured to allow gas molecules to move through it but at a relatively slow rate including materials such as polymers, nano-layer composites, organic and inorganic films, crystals, sintered and compacted particulates, and the like.

The mechanism for the gas moving through the interface layer may include diffusion, permeation, molecular flow, active transport, osmosis, orifice flow, and any other mechanism of flow relating to gas molecules penetrating a restrictive or molecular-species dependent barrier. In the case of an interface layer that is formed from a material through which diffusion, permeation, or molecular flow is the dominant process, the concentration gradient or partial pressure gradient is the primary driving mechanism in the gas evolution rate. For interface layers where orifice flow is the dominating term, the orifice geometry combined with the internal and external pressures determine the gas evolution rate over time. For interface layers using active transport or other flow mechanisms, similar rationales apply. In principle, any of these generalized processes can be incorporated, singly or in combination, into a particular gas package design, with the particular combination being selected or designed based upon the requirements of the final application. If desired, the interface layers preferably allow only the uni-directional flow of gases. The determining factors for the gas evolution rate of a particular gas package design can be determined such that the interface layer ultimately can be characterized based upon one or more of the above principles, singly or in combination. Such methods of characterization may include simulation, empirical testing, and other similar methods.

The interface layers also may have the property that the desired therapeutic gas preferentially may be conducted through the interface layer when compared to other gas species that may be present within the gas package's reservoir or in the environment where the gas package will be used, possibly including gases or liquids encountered at the time and point of treatment. Such preferential flow behavior is demonstrated by molecular sieves, nano porous structures, various polymer membranes, and many other materials. Utilizing such materials as interface layers in order to take advantage of this preferential behavior may be optionally selected for some gas package devices where it is preferable to isolate gas species.

In regards to gNO, the interface layer material may be any suitable polymer, especially the ones disclosed in the articles, "The transport of nitric oxide through various polymeric matrices," K. A. Mowery and M. E. Meyerhoff, Polymer Communication, 1999, p. 6203-07, and "Amperometric nitric oxide gas sensor: preparation of Au/SPE and sensing behavior," Jing-Shan Do and Kanq-Jiuan Wu, Sensors and Actuators B 67 (2000), p. 209-16, which are incorporated herein by reference in their entirety. The polymer suitable for certain gNO-emitting gas packages according to the present invention may be selected by the polymer diffusion rate, several of which are described in the Mowery and Meyerhoff article.

As used herein, "sealing layer" is an impervious layer that covers all or some portion of an interface layer, and may be removed or otherwise compromised in order to activate the gas package and begin the delivery of therapeutic gas from the package's reservoir to the external environment. The sealing layer may prevent gas from transiting the interface layer until it is compromised. The sealing layer of a gas package may or may not be a discrete element of the device because, for example, it may form part of or be incorporated into the holding container.

As used herein, "delivered gas" is any therapeutic gas, or combination of therapeutic gases, the molecular flow of which is desired to be controlled. "Delivered gas" can include, but is not limited to, gaseous nitric oxide (gNO), oxygen ($O_2$), carbon monoxide (CO), nitrogen ($N_2$), nitrous oxide ($N_2O$), and any other therapeutic gas the molecular flow of which is intended to be controlled. The delivered gas may be selected on the basis of the intended treatment performed by or use of the gas package. For example, $N_2O$ may be selected for use in a gas package in order to provide local pain management at an open lesion, burn, or wound. The therapeutic gas also may be a sterilizing gas, meaning a gas that is capable of sterilizing an object, surface, or volume or that at least is capable of maintaining or creating an environment that is hostile to pathogens.

As used herein, "holding container" is a container intended to protect and keep the gas package in a state of "no change" or "ready for use." The holding container, rather than being a separate, discrete device or element, optionally may form part of or incorporate a sealing layer. Preferably, the holding container is permanently impermeable to the therapeutic gases so that no substantial gas evolution is capable of occurring until the holding container is opened or compromised. The holding container also preferably is rigid and durable so that it is capable of providing a degree of physical protection to its contents.

As used herein, "gNO package" is a special case of gas package wherein the delivery gas is gNO.

As used herein, "gNO" is gaseous nitric oxide (NO), or gaseous NO diluted in an otherwise inert carrier gas, especially but not limited to inert carrier gases such as nitrogen ($N_2$).

As used herein, "gas patch" is a gas package that is configured as a bandage-like layer wherein the reservoir and interface layers are thin and broad, to allow delivered gas to be delivered from one or more surfaces.

As used herein, "sterilize" is the action of either maintaining a sterile state or creating a sterile state by killing non-desirable pathogens. This term also may include the act of or intention to disinfect or provide the feature of disinfection. Therapeutic gases that may be delivered by use of the gas packages described herein include gases that are capable of sterilizing an object, volume, enclosure, or at least creating an atmosphere inhospitable to non-desirable pathogens, regardless of the therapeutic gases' potential beneficial or "therapeutic" effects on animal and human bodies.

As used herein, "activate" is the act of removing, compromising, or otherwise defeating the sealing layer and/or holding container, possibly in conjunction with removing the active elements of the device from the holding container, such that the delivered gas is evolved.

As used herein, "treatment" is the act of applying and activating the gas package in such a manner as to affect the proscribed gas delivery to the intended target for the intended period.

A gas package can achieve the controlled delivery of one or more therapeutic gases by inducing a mass flow of gas molecules through a properly configured and designed interface layer between a known source concentration of gas (alternately, with a known partial pressure) and the intended delivery location at a situs on or in the body or elsewhere with a zero or much lower concentration of gas (or alternately a zero or much lower partial pressure). Therefore, the gas packages described herein operate under the principle that the interface layer can be configured to allow gas molecules to migrate across the layer from the gas package's reservoir to the desired treatment site. The gas concentration gradient between the reservoir of gas and the target situs and the overall evolution of delivered gas at the target situs can be provided in an arbitrarily large number of combinations.

The rate of gas evolution can be controlled by utilizing one or more flow restricting mechanisms such as: (1) a diffusion layer or layer composite, including arrays or panels of layers to achieve the desired delivery profiles and to spatially isolate or localize delivery; (2) selective flow or permeation through micro orifices, arrays of micro orifices, woven or stitched fabrics, molecular flow channels, and molecular sieves, optionally arranged in panels or arrays to spatially isolate or localize delivery; and (3) other mechanisms operating on the nano or micro scale using principals of mass transport. The delivery profile of gas (e.g., gas flow rate and temporal duration) from the gas packages can be controlled by careful selection among different design factors in order to create gas packages that deliver gases with specified, unique delivery profiles. These factors include, but are not limited to, the gas concentration/partial pressure in the reservoir, the relative pressure of the reservoir, the reservoir volume, the interface layer design, the number of gas packages, whether the gas packages are operated serially or in parallel, and so forth.

The delivered gas that is evolved from the gas package may be applied directly to the target site (e.g., as in a wound dressing configuration), may be dissolved into a carrier stream that carries the gas to the target site (e.g., in inhaled applications and blood treatments), or may flood an area or volume within which the target site is contained (e.g., in sterilization and topical application). One or more interface membranes or materials may be selected to act in combination with selected source pressures and concentrations and optionally source gases and source gas mixtures to deliver prescribed gas concentrations or flow rates of gas at desired locations. In this way, the gas packages described herein may be used to treat medical and non-medical conditions in the body that are susceptible to treatment using therapeutic gases such as, but not limited to, gNO, $O_2$, CO, $N_2$, and $N_2O$. Treatments using the gas packages may consist of one or more staged exposures delivered as part of a treatment sequence.

A number of methods may be used for providing or generating the source of gas required to operate the gas packages, including but not limited to: storing the gas, or a gas containing gas mixture, as a compressed gas in a cylinder or other macroscopic vessel, optionally discharge by means of a pressure or flow regulator; storing gas at high concentrations and at pressures approximating atmospheric pressure; storing gas in a dense matrix of cells formed in materials, composites, or constructs with high-surface-area-to-volume micro or nano structures; storing gas in a material or composite comprised of a large number of small volumes, for example in the manner of a foam or sponge structure, wherein each small volume contributes to the total volume available for storage; storing gas in a pseudo-closed cell arrangement, in which case the cells also may contribute to the restriction of gas evolution, or alternately storing gas in an open cell arrangement in which case the cells will have a lesser effect on the restriction of gas evolution; storing gas at a molecular level as an adsorbed or absorbed gas, on or near a material surface such as very thin materials that have been highly folded and materials that have been sintered or compacted out of small particles such that the relative surface area for a given volume is increased and channels for the gas to enter or exit the bulk material are provided; producing gas at the point and time of use by direct or indirect chemical reaction in the reservoir of the gas package, for example, by breaking a pouch or ampoule to allow two chemicals to mix inside the reservoir which in turn react and produce the gas; and producing gas at the point and time of use by thermal activation or thermal decomposition, for instance, by using an electric or chemical heat/thermal energy source. Various similar means for providing or generating the desired gas are known in the art. The particular method of gas storage or production suitable for a particular gas package is dependent on the fit and functional requirements for the final application the package is intended to support.

Advantageously, the intended gas can be selected from a wide range of candidate gases in accordance with the underlying operation of the gas packages described herein. This is a particularly relevant advantage over polymer-based therapeutic gas delivery devices since the chemical structure of the polymer determines which gases may be entrained or evolved, thus often necessitating a different polymer formulation for different gas species.

Preferably, the therapeutic gas that is to be delivered using the gas packages described herein is gNO. The administered dose of gNO depends upon the desired effect, the duration of gNO exposure and the conditions of the materials or tissues being treated. For example, in situations where gNO is being delivered as a preventative measure, gNO may be administered at different rates and durations than would be used in situations where an existing disease or other condition already is known to exist.

Where gNO is the delivered gas, the typical dosage for inhaled applications range from about 1 ppm to above about 300 ppm, with doses from about 10 ppm to about 200 ppm being preferred. For other applications such as topical treatments to the skin or for sterilization applications, concentrations can range into the many tens of thousands of ppm. Preferably, the gas packages are capable of delivering gNO at rates equivalent to less than about 1 ppm to over about 50,000 ppm of exogenous gNO. Even more preferably, the gas packages are capable of delivering substantially pure gNO to an animal or human subject. The gas packages also preferably are capable of delivering gNO over short treatment duration times on the order of minutes, but also for longer treatment duration times as dictated by the particular application, for example on the order of weeks, months, and years.

The gas packages disclosed herein have many different beneficial uses because of their ability to deliver therapeutic gases to situs in or on the bodies of animals and humans including, but not limited to, the skin, respiratory airways such as the upper nasal system and sinuses, eyes, rectum, vagina, face, mouth, and the like. In general, the gas packages are capable of performing treatments of any type of condition that is susceptible to prevention, treatment, or alleviation with therapeutic gases. Some exemplary uses of the gas packages in regards to incipient or existing diseases and conditions include, but are not limited to: treating vasodilatation; destroying and inhibiting bacterium; destroying and inhibiting viruses; destroying and inhibiting fungi; destroying and inhibiting biofilms; preventing and treating respiratory conditions and diseases; preventing and treating airway, eye, and ear infections and conditions and to act in an anti-mucolytic capacity; preventing wound infection and treating existing wound infections; promoting wound healing by reducing biofilms and enhancing circulation; treating burns and accelerating burn recovery; treating cosmetic conditions (e.g., acne and cosmetic wounds following surgery); and as a cancer treatment or cancer therapy support treatment (e.g., for treatment of skin cancer). The gas packages also have the additional capacity to act as a sterile bandage or wound cover with the ability to return to a sterile state if the bandage is contaminated on application or upon use. The capability of the gas packages to perform these treatments and other functions depends in part on the delivered gas, and gNO is a preferred delivered gas for these purposes.

Different applications of using the gas package device include, but are not limited to: topical treatments, cosmetic applications, treatment of vasodilation conditions, inhalation treatments, treatments of the blood, treatment of the skin or tissue, treatment of infections, treatment of inflammation on or within the body, and treatments of biofilms. Other conditions, aliments, or symptoms that may be treated with therapeutic gases delivered from the gas package device include bronchoconstriction, reversible pulmonary vasoconstriction, asthma, pulmonary hypertension, adult respiratory distress syndrome (ARDS), and persistent pulmonary hypertension of the newborn (PPHN). Topical treatments may include treatment of wounds or surface infections. The gas packages therefore are not limited by the type of treatment that is contemplated.

One or more treatments, delivery methods, delivery devices, and applications described in the following patents and patent applications, each herein incorporated by reference in its entirety, may benefit from the delivery of therapeutic gases from the devices described herein: U.S. Ser. No. 11/497,557; PCT/US05/016428; Ser. No. 11/445,965; Ser. No. 11/211,055; Ser. No. 11/591,373; Ser. No. 10/615,546; Ser. No. 10/658,665; Ser. No. 11/445,965; Ser. No. 11/066,790; Ser. No. 10/953,827; Ser. No. 11/592,950; Ser. No. 10/315,539; Ser. No. 11/158,902; Ser. No. 10/269,738; PCT/US05/016427; Ser. No. 11/021,109; PCT/US05/047319; PCT/IB06/0003265; 60/810,938; Ser. No. 11/107,618; PCT/US06/14414; Ser. No. 10/615,546; Ser. No. 11/591,373; U.S. Pat. No. 6,920,876; U.S. Pat. No. 7,122,018; U.S. Pat. No. 5,485,827; U.S. Pat. No. 5,873,359; U.S. Pat. No. 6,432,077; and U.S. Pat. No. 6,793,644. Additionally, the treatments described in U.S. patent application Ser. Nos. 11/704,791, "Use of Gaseous Nitric Oxide Gas As An Anti-Cancer Agent", 11/704,602, "Use of High Dose Concentrations Of Gaseous Nitric Oxide," and 11/591,373, "Method and Apparatus For Treatment of Respiratory Infections By Nitric Oxide Inhalation," all incorporated herein by reference in their entirety, may benefit by the delivery of gNO from the devices described herein.

The gas packages may be secured to an animal or human patient using, for example, an adhesive that is capable of securing the gas package to the patient. Alternatively, the gas packages may be secured to a patient, and especially irregular portions and shapes on a patient, using a wrap. In another alternative, the gas package may be configured (i.e., fabricated) as a fitted garment for application, for example, to an appendage or limb of an animal or human patient. In still another alternative, the gas package device may be configured (i.e., fabricated) as a wrap so the device is capable of being fitted over irregular shapes. In yet another alternative, the gas package device may be configured as a suppository for insertion into a body orifice including, but not limited to, the anus, vagina, mouth, nose, ear, and urinary tract.

The gas packages also may be used for sterilization purposes, i.e., to prevent or inhibit contagions from becoming established in a patient. In situations where exposure to contagious elements is possible or expected, the gas packages can be employed as part of a suite of sterilization protective measures. For example, the disclosed gas packages may be used to create or maintain a sterile condition or to create conditions notably hostile to contagious agents in or on: a nasal cannula and a nasal cannula delivery device; a protective face mask or respiratory filter, wherein the gas package maintains a sterile field whether the mask or filter is in use or in storage; a field dressing for emergency first aid situations to prevent a wound from becoming contaminated or to start infection control treatments as soon as possible; bandages such as a wound dressing for wounds receiving controlled treatment programs; respiratory therapy or breathing support equipment, especially the internal conduits and channels used to conduct breathing gas to and from a patient or to sample or monitor the gases being delivered or returned from a patient; a patient protective or quarantine enclosure used to isolate infectious or immunodeficient patients; a protective cover over a portion of or in the body, possibly acting as a wound treatment enclosure; covers, shrouds, and protective packaging over medical devices or equipment, or in a cavity within a piece of medical equipment; medical waste, used instruments, contaminated clothing, soiled linens, bedding, equipment and similar contaminated materials which have been collected into comparatively air tight packages such as a bags, boxes, and other such containers for treatment with an appropriate gas; animal and human remains that may be contaminated or carry contagions; body fluids that may be contaminated or carry contagions; and large enclosures, rooms, and other spaces when the gas packages are in larger sizes or formats, or when a number of smaller gas packages are used in parallel or in succession.

In particular, the gas packages advantageously may be utilized as part of sterilization or disinfection regimes in a wide variety of situations where it is impractical to use conventional sterilization techniques. Because gNO has the ability to kill dangerous pathogens, a gNO package is a preferred gas package for the purposes of creating and maintaining a sterile condition.

For any of the foregoing treatment, alleviation, and prevention purposes, the simple principal of operation and corresponding ease of use makes the gas packages ideal for wide scale deployment to and use by lay persons, especially in situations where large numbers of patients may need to be treated in a short period of time. These situations cannot easily be addressed by conventional therapeutic gas delivery systems since they are more complex, require specialized training to use, and need regular service and maintenance.

The gas packages described herein have many different advantageous features or properties. For example, the gas packages preferably can be manufactured to be disposable without creating unusual safety hazards. Also, the gas packages preferably release the delivered gas without also releasing secondary products that may produce undesirable side effects. The gas packages may be very simple to construct and use. In terms of use, the gas packages are less cumbersome than a conventional delivery system because they can be made to be physically smaller and can be utilized without having to set up or operate sophisticated equipment. Another potential advantage of the gas packages is that, unlike polymer-based gas delivery devices, the gas packages are not dependant on gas absorption characteristics of a polymer substrate and can be configured to deliver gas over a wide range of mass flow and time. A potential advantage of gNO packages in particular vis-à-vis polymer-based gNO delivery devices is that the presence of moisture is not required for evolution of the gNO, thus reducing the potential for the formation of nitric acid.

Described now are various examples of the gas package devices described herein. Although the gas packages are described in terms of the delivery of any therapeutic gas, it will be appreciated that the devices especially may be adapted for the preferred purpose of delivering gNO in accordance with the description herein.

EXAMPLES

Example 1

FIG. 1, embodiments A-G, illustrates an exemplary gas package. Embodiments A-C illustrate, respectively, side, top, and end views of a holding container 11, which is part of the illustrated gas packaged. Embodiments D-F illustrate, respectively, side, top, and end views of the remainder of the device held within the holding container. Embodiment G illustrates an exemplary multi-patch configuration of the device.

The holding container 11 of the gas package includes optional flange portions 16 on two sides of the container. The flange portions 16 are convenient surfaces by which a user may hold the holding container 11. The holding container preferably is a substantially sealed container for holding the remaining elements of the gas package for long-term storage. The holding container also preferably is rigid and durable so that it is capable of providing a degree of physical protection to its contents.

The gas package also comprises an interface layer 15 that defines a reservoir 18 that is provided with a charge of one or more therapeutic gases, preferably including gNO. The combination of the interface layer 15 and the reservoir 18 may be referred to as a gas patch. Surrounding the gas patch, an optional gauze layer 17 may be provided. The gauze layer 17 may be preferred in order to make the gas patch appear similar to a traditional bandage or wound dressing, and to impart some of the functionality of a traditional bandage or wound dressing to the gas patch. The gas package also comprises a sealing layer 14 that surrounds the optional gauze layer 17 and the gas patch (e.g., the interface layer 15 and reservoir 18).

As illustrated in embodiment D, the sealing layer 14, rather than forming a tight, snug seal over the interface layer 15, instead seals a volume between the interface layer 15 and the sealing layer 14. In this configuration, gas will be able to pass from the reservoir 18 through the interface layer 15 into the volume between the interface layer 15 and the sealing layer 14 until an equilibrium concentration or pressure of gas is achieved, given sufficient time and assuming the sealing layer 14 is left in place. Gas will be prevented from passing through the sealing layer 14 to the external environment until the sealing layer 14 is compromised and the holding container 11 is opened. In an alternative configuration, the sealing layer 14 forms a tight seal over the interface layer 15 (e.g., by means of an adhesive), optionally sandwiching the gauze layer 17 in between the sealing layer 14 and the interface layer 15 so that the sealing layer 14 must be removed before gas is able to physically pass from the reservoir 18 through the interface layer 15 to the external environment.

The device may be activated by opening the holding container 11 and compromising the sealing layer 14, such as by breaking or otherwise causing a hole to be placed into the sealing layer. In the case where the sealing layer 14 defines a volume between the sealing layer 14 and the interface layer 15, activation of the device causes an immediate outflow of gas from the volume between the sealing layer and the interface layer, thus producing a gas concentration gradient across the interface layer 15 that previously was in equilibrium due to the entrainment of gases on the external side of the interface layer by the sealing layer. Upon activation, gas begins to flow out, or evolve, through the interface layer 15 from the reservoir 18 to the external environment.

Figure 1E:
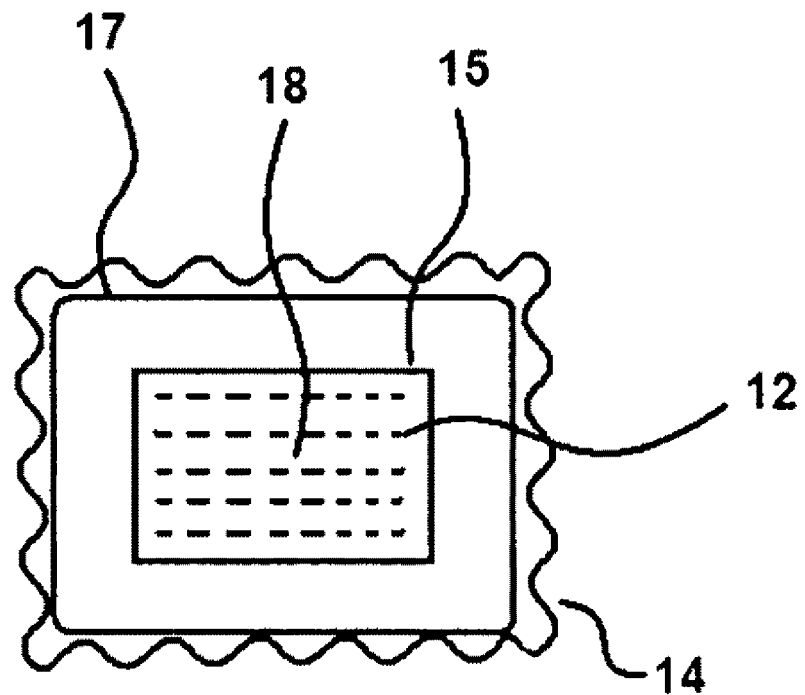
Figure 1F:
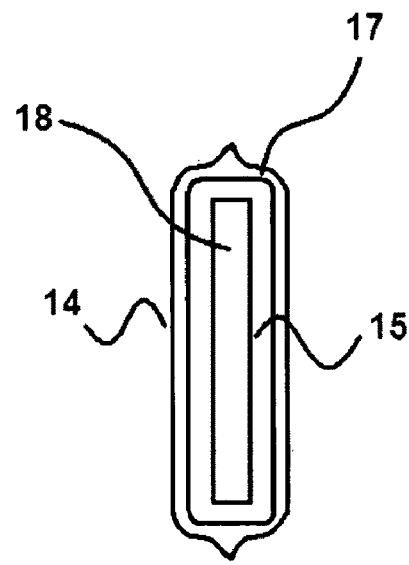

Many possible construction geometries are possible including planar arrangements, co-axial or cylindrical shapes, pouches, beads, flexible laminations as well as many others. In order to maintain its shape when internally pressurized, certain structural tension members or other designs optionally may be incorporated into the devices. For example, if this is constructed from fabric materials, quilt stitching or bonding 12 as illustrated in FIG. 1E, can serve to prevent the device from being distorted from its intended shape. In the case of non-planar geometries, ribs, flanges, internal wires, and other structural elements well known to the art could be used.

Figure 1G:
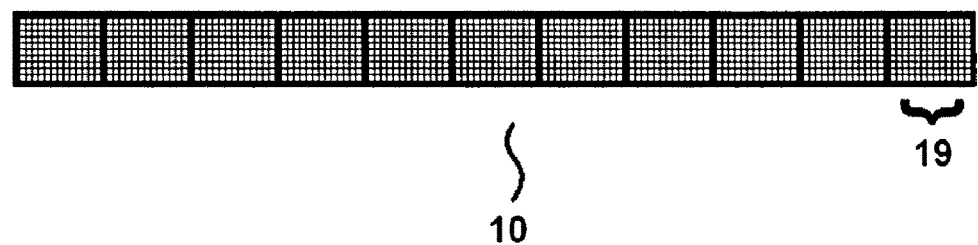

FIG. 1G illustrates an exemplary device wherein many gas patches 19 with an optional gauze covering are combined into a single element 10. As depicted in FIG. 1G, the element 10 has been removed from its holding container and sealing layer, thus exposing the optional gauze layer. The gas patches 19 may be perforated at their edges in order to aid in detaching the patches from one another. An element 10 such as this may be packaged, for example, in a cylindrical holding container wherein the element 10 is wound into a tight roll for convenient, compact storage. The element 10 provides a user-configurable treatment device; gas patches 19 may be used individually or, if so desired by a user, may be used in plurality. The user, for example, if desiring a device of a certain length, can tear or cut a bundle of gas patches 19 of an appropriate length off of the remainder of the element 10. Thus, the element 10 provides a device for the delivery of therapeutic gases in a user-configurable length. For example, element 10 may be especially useful to wrap a portion of a body or appendage.

An exemplary use of the gas packaged illustrated in FIG. 1 is that of a sterile bandage or wound cover that has the capability to return to a sterile state if the bandage is contaminated during application or use thereof.

Example 2

Figure 2A:
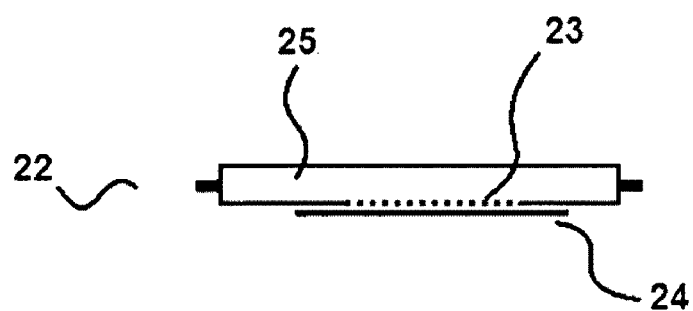
FIG. 2, embodiments A-C, illustrates another exemplary gas package.
Figure 2B:
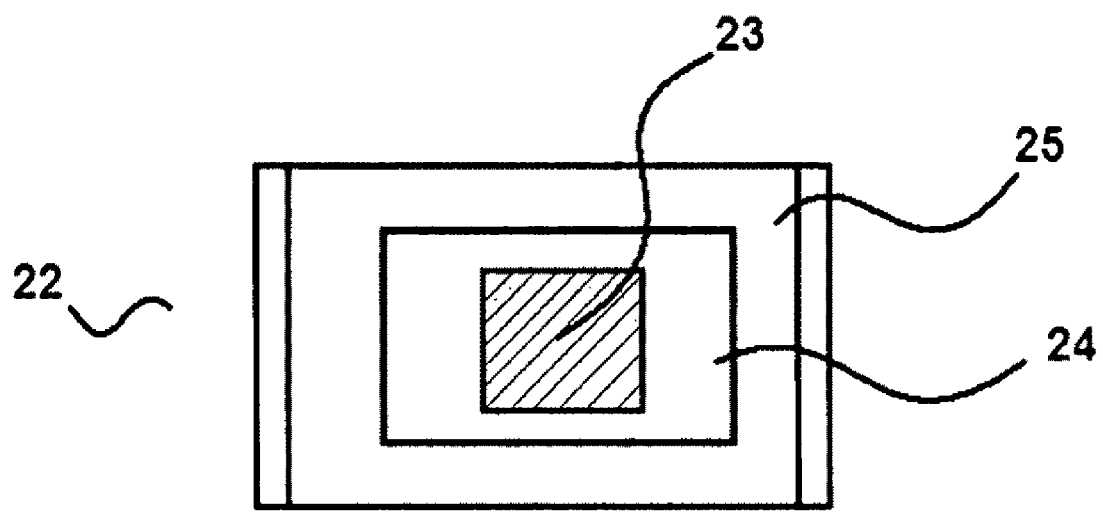
Figure 2C:
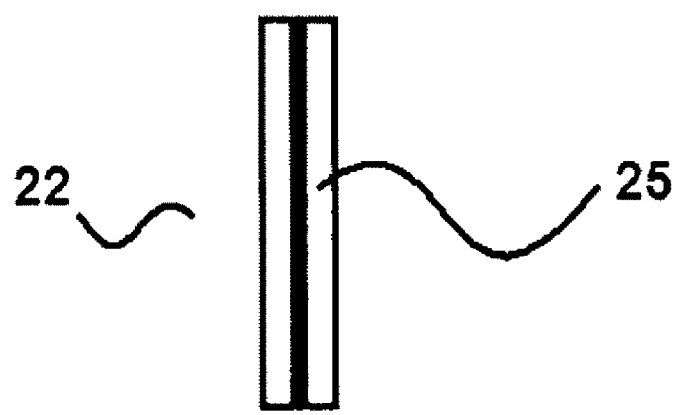

FIG. 2, embodiments A-C, are respectively top, front, and end views of a gas package 22 wherein part of the reservoir structure 25 also forms part of the holding container. In this configuration, the interface layer 23 initially is covered by a sealing layer 24 that prevents the outflow or evolution of gas until the sealing layer is removed or compromised in order to expose the interface layer 23, thus activating the gas package 22. Preferably, the sealing layer 24 is secured to the interface layer 23 and reservoir structure 25 by an adhesive that is sufficiently strong to secure the sealing layer 24 but also sufficiently weak to allow the sealing layer to be removed without damaging either the interface layer 23 or reservoir structure 25. In an alternative, the sealing layer 24 or a portion thereof may be intended to be removed by scraping it off of the interface layer 23, for example using a fingernail or coin. As seen in FIG. 2A, the reservoir structures 25 has flanges on either side for ease of use; the flanges are convenient surfaces by which a user may hold the gas package 22. The device illustrated in FIG. 2 may be especially desirable where the direction of the flow of delivered gas is desired to be controlled. The interface layer 23 depicted is located on only one side of the gas package 22. Gas is delivered only through the side of the package 22 having the interface layer because the holding container prevents gas from flowing out of the device's other sides; thus, the delivery of therapeutic gas is restricted to a certain direction (i.e., unidirectional).

Example 3

Figure 3:
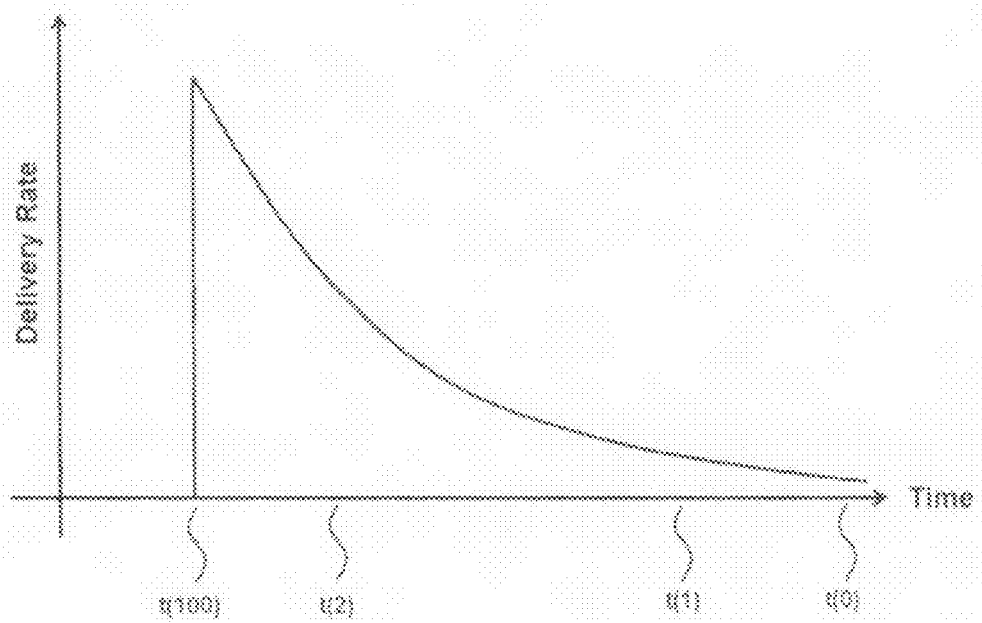
FIG. 3 is an exemplary plot of the rate of evolution of gas across the interface layer of a gas package.

FIG. 3 is an exemplary plot of the rate of evolution of gas across the interface layer. Prior to activation, the concentration of gas in the gas package is constant since the constituent gas is trapped within the reservoir. When delivery is desired, the impermeable holding container is opened and/or the sealing layer is removed or otherwise compromised and the pressure and/or concentration gradient between the reservoir and the external environment causes gas molecules to migrate across the interface layer, driven by diffusion, permeation, or simply pressure, consistent with the mechanisms of the interface layer that have been described. Activation, indicated by time t(100), typically is the time of the peak gas evolution rate. At some time t(0), the reservoir is substantially exhausted and gas evolution essentially ceases.

In the intermediate period between times t(100) and t(0), and to a first approximation, the decay in the evolution rate is dominated by an exponential term with a delivery constant that by design can be made longer or shorter. More resistive interface layers and larger reservoirs will provide for longer delivery times. Higher source concentrations or pressures can provide higher initial evolution rates. Selection of interface layer resistance, reservoir volume, and initial reservoir concentration and pressure fill therefore can control the evolution characteristics. The apparent shape of the delivery curve and the delivery rate in general also are dependent on the concentration of gas at the targeted treatment site. As the delivery side concentration rises (i.e., the concentration of gas in the environment external to the reservoir of the gas package), the gradient across the interface layer is reduced by a corresponding amount. For high reservoir concentrations and/or pressures, the magnitude of the concentration or pressure of the gas on the treatment side has less of an effect on the exponential delivery behavior.

Time t(2) is the time where the gas package is first applied to perform the desired treatment. In some cases it may be advantageous to allow the device to evolve gas for a period of time before applying the device to the treatment site or application, so as to allow the gas evolution from the interface layer to reach a quasi-equilibrium state and to also allow for the interface layer to condition. Conditioning may include saturating the interface layer with gas or allowing undesired or contaminating gases entrained on the surface of the interface layer to be forced out of the device. Time t(1) is an optional time when the gas package is to be removed from the treatment location so that gas delivery can be terminated. The description herein provides the means whereby the design of the interface layer or materials, the pressure of the gas in the gas package reservoir, the concentration of gas in the gas package reservoir, and the volume of the reservoir work are able to work in combination to allow the delivery of gas to be predicted and controlled and whereby the rate of diffusion of gas across the interface layer can be established to achieve specific delivery profiles for the gas. If desired, the gas package can be designed so that the change in delivery rate between t(2) and t(1) is negligible (i.e., near a constant delivery rate of gas).

Example 4

Figure 4:
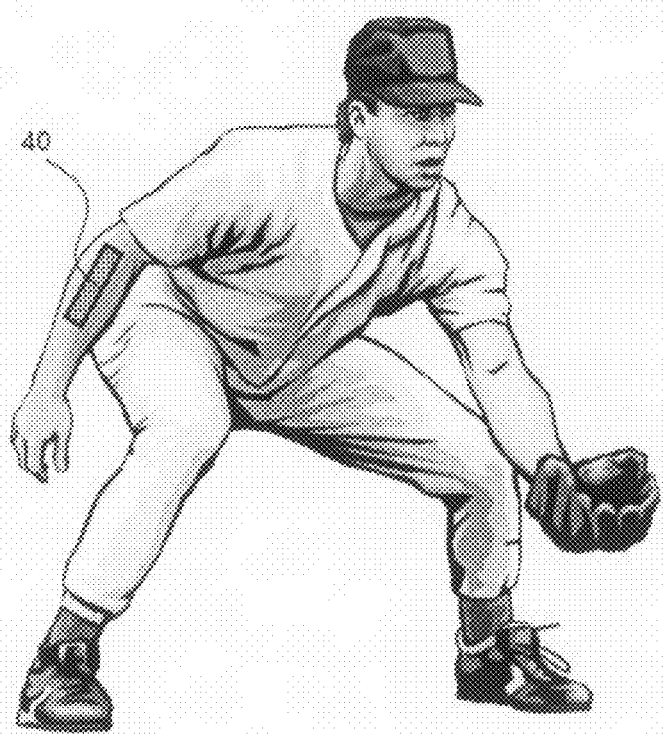
FIG. 4 illustrates the placement of a gas package on a human body.

FIG. 4 illustrates that the gas package 40 can be placed on any location on or in the body where a therapeutic gas is to be delivered. A gas package can be used on the surface of the body in the fashion of a wound dressing, bandage, gauze, sheet, or other similar implementation using suitable adhering means, such as materials and adhesives that adhere to the skin, elastic wraps, tape, and ties. Bandage-style applications are desirable for use in connection with, for example, the treatment of open lesions, burns, grafts, and other large surface area sites where it is desired to leave the wound open for proper treatment but where a sterile field needs to be maintained.

Alternatively, the gas package may be contained within or form part of garments such as socks, cuffs, gloves, shirts, pants, gowns, protective suits, and the like. In another alternative, the gas package is formed as an elongated bandage wrap so that it can be positioned around larger portions of the body including, but not limited to, the head, the face, the chest, limbs, and joints, thus treating a large body area. An elongated bandage may be advantageous to the patient because of its comfort, ease of use, and wide variety of uses. The wide variety of ways in which a gas package may be configured means that the packages are capable of being used by a wide variety of patients with differing body sizes and treatment needs.

In a preferred alternative, the gas package is configured as a gas patch held or positioned within a patient. For example, the gas patch may be placed in the mouth to treat teeth, wounds, lesions, cavities, and the like. gNO in particular is suitable for treating dental conditions because of its anti-inflammatory and antimicrobial effects. Reduction in inflammation in the mouth, gums, and the like can lead to the reduction of pain and associated discomfort. gNO may thus be suitable to treat any of the dental conditions described in WO 2005/046660, "Modulating Substances of the Nitric Oxide (NO)-Cyclic Guanosine-3',5'-Monophosphate (cGMP) Signaling Pathway for the Treatment of Dental Disorders," herein incorporated by reference in its entirety.

In another alternative, the gas package in configured as at least part of an eye patch or goggles for treating eye infections or contamination. The gas package also could be configured, for example as a sponge-like, compressible plug, for placement into a nose or ear to treat localized infections.

In a preferred device, the gas package may be configured as a wound dressing. A gas package configured as a wound dressing may be especially useful for maintaining, or alternatively creating, a sterile environment at a wound situs. For example, where a burn has occurred or an incision has been made into a subject, a gas package configured as a wound dressing may be applied to the burn or incision in order to maintain the sterile field or, if not yet created, to create a sterile field. The gas package is capable of accomplishing this by emitting a sterilizing gas, preferably gNO, in the vicinity of the wound to which the dressing is applied. In the case of gNO, it may be preferred to apply the gas package-wound dressing after bleeding has stopped because gNO is capable of causing vasodilatation and increased bleeding.

Gas packages configured as wound dressings especially may be useful in combat situations where the creation and maintenance of sterile conditions at the site of a field wound is important due to the limited medical response available. Thus, the use of gas packages configured as wound dressings may increase the likelihood of a proper recovery following a combat wound.

The gas packages configured as wound dressings may be packaged, for example, with other wound-treatment devices or compounds so that the gas packages may be used in conjunction with the other devices or compounds. For example, the gas packages may be packaged with an Israel-type tension band. The tension band may be used to stop bleeding, after which or in conjunction with which the gas package may be applied to create and/or maintain a sterile field at the site of the wound. Cauterizing agents (e.g., chemical cauterizing agents in the form of a powder that can be applied to a wound) and blood coagulating agents (e.g., chemical coagulating agents that can be applied to a wound) also may be packaged with a gas package for use in combat-type and other emergency situations. Combining a gas package-wound dressing device with a device or agent for stopping or preventing bleeding especially is desirable where the delivered gas from the gas package is gNO or another gas with vasodilatory properties.

The gNO packages described herein also may be configured as, or incorporated into, tension bandages so that the tensioning of the bandage stops bleeding even in the presence of the vasodilatory gNO, thus enabling the immediate application of gNO to a wound without waiting for bleeding to stop. One or more gNO or other gas packages generally described herein may be incorporated into such tension bandages.

A number of other exemplary gas package configurations and delivery profiles associated with the gas packages are shown in FIGS. 5, 6, 7, and 8.

Example 5

Figure 5:
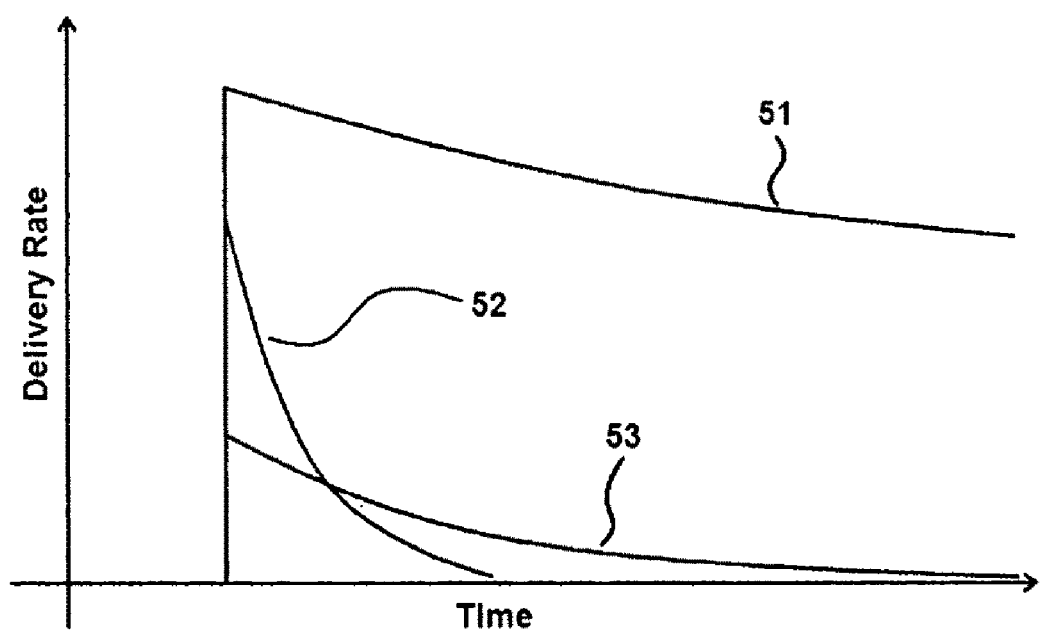
FIG. 5 illustrates three exemplary delivery rate curves.

FIG. 5 illustrates three exemplary delivery rate curves 51, 52, and 53. The three delivery rate curves correspond to three different desirable treatment scenarios or regimes, which can be selected from in accordance with the therapeutic needs of the patient or other individual who is to be treated.

Consider for example, the delivery rate curve 51 in FIG. 5. This exemplary delivery rate curve corresponds to a device equipped with a comparatively large reservoir volume, a very resistive interface layer, and a high initial gas concentration. As shown, the initial gas evolution rate will be relatively constant, that is, the delivery rate will be slow enough that the initial delivery appears either flat or possibly linear. If this configuration is used in a medicinal application, the device will provide for a fairly constant gas dose or delivery over a period of time. This type of approach may be desirable if the treatment scenario requires relatively constant and high dosage gas exposure. At a predetermined time, the device potentially could be exchanged for a fresh unit to extend the period of constant delivery. A device having a delivery rate curve similar to that shown in 51 may be useful, for example, in connection with routine wound dressing changes.

A second useful scenario shown in FIG. 5 is delivery rate curve 52. In this exemplary delivery rate curve the goal is to provide a short duration, high rate delivery. This exemplary delivery rate curve corresponds to a device equipped with a moderately resistive interface layer and a moderately sized reservoir filled with a moderate concentration of gas. This configuration of the device may provide for an initial high dosage rate that slows quickly to a substantially inert dosage rate. The initial bolus of gas could be used, for example, to sterilize, disinfect, or otherwise saturate an administration site with gas. This delivery profile especially may be desirable where the gas packaged is used in a gas mask and delivery of gas is desired over a shorter period of time.

A third useful scenario shown in FIG. 5 is delivery rate curve 53. This exemplary delivery rate curve corresponds to a device equipped with a small reservoir filled with a moderate concentration of gas and a very resistive interface layer. This configuration of the device may provide for a low but relatively steady dose of gas for an extended period of time corresponding to the device's useful life. Devices such as this may be useful as packaging inserts or components of sterile products because the slow release of gas may result in an inhospitable environment within a sterile package that inhibits bacterial and viral colonization.

One of skill in the art will recognize that other gas package configurations may achieve delivery rates similar to those depicted in FIG. 5, in accordance with the description herein.

Example 6

FIG. 6, embodiments A-H, illustrates an exemplary multi-reservoir gas package containing an array of sealing layers and isolated gas reservoirs. A multi-reservoir gas package, for example, may be useful in an inhaled-gas application, wherein the delivered gas would be swept up by each breath and introduced into the patient's lungs and airways and where the dose might need to be maintained at a relatively uniform level for a time period and then drop off quickly at the end of the treatment.

In this exemplary device, the individual unactivated reservoirs 62 can be activated in succession 61 by removing segmented sealing layers that define the reservoir volumes in order to achieve an extended dose period or to refresh the source gas concentration. As each individual reservoir is activated, the gas contained therein is released in a controlled manner. Alternatively, however, segmented interface layers also may be provided so that, upon removal of a segmented sealing layer, the gas contained in the reservoir is released through the interface layer. The alternative use of segmented interface layers may result in a more smooth or constant delivery rate curve compared to a multi-reservoir device that does not comprise an interface layer.

In another alternative configuration, the exemplary device illustrated in FIG. 6, instead of having segmented sealing layers, can have a continuous sealing layer enclosing the gas reservoirs. The gas package can be activated by piercing the continuous sealing layer at the location of the individual reservoirs in a prescribed fashion. For example, the sealing layer could be punctured using a needle at the location of an individual reservoir in order to activate that reservoir. This process can be repeated for each reservoir in the gas package until all of the reservoirs have been activated. Alternatively, the gas package can be activated by peeling back the continuous sealing layer in order to rupture the individual reservoirs in a prescribed fashion.

Example 7

Figure 7:
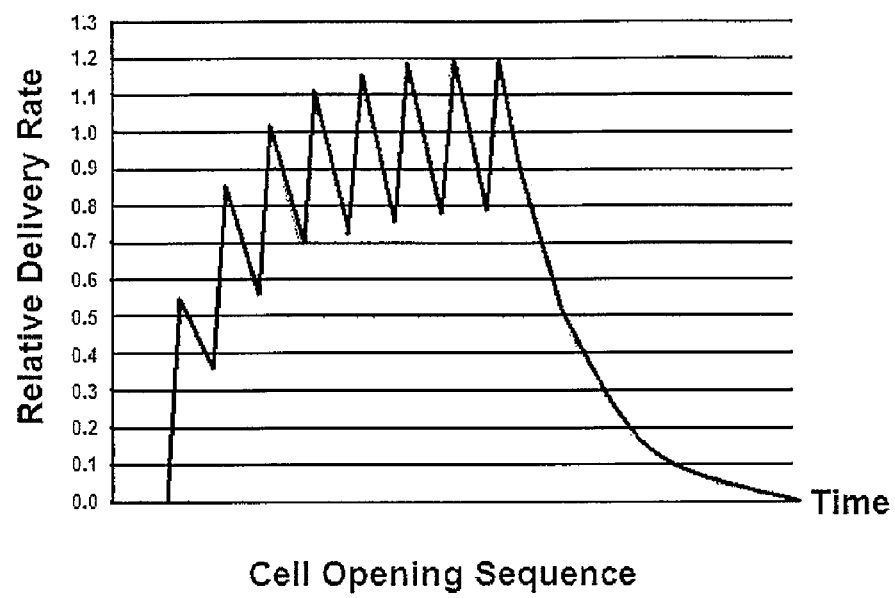
FIG. 7 illustrates an exemplary delivery rate curve corresponding to a multi-reservoir gas package.

FIG. 7 illustrates an exemplary delivery rate curve corresponding to the exemplary multi-reservoir gas package illustrated in FIG. 6. The troughs in the delivery rate curve correspond to the time of activation of individual gas reservoirs in the gas package. As each individual reservoir is activated, the gas is released from the individual reservoir, thus causing an increase in delivery rate followed by a subsequent decrease in delivery rate in the fashion described until activation of the next reservoir. The activation process may be repeated multiple times depending upon the number of individual reservoirs in the device. For example, in this exemplary delivery rate curve eight troughs are illustrated (including the initial activation at rate 0.0) corresponding to the prescribed activation of the eight individual reservoirs in the exemplary multi-reservoir gas package illustrated in FIG. 6. Although depicted in FIG. 7 as occurring at semi-regular time intervals, activation of the individual reservoirs of a multi-reservoir gas package also may occur at irregular intervals and more than a single reservoir may be activated at a time. Thus, the exemplary multi-reservoir gas package provides additional dosage rate flexibility.

Example 8

Figure 8:
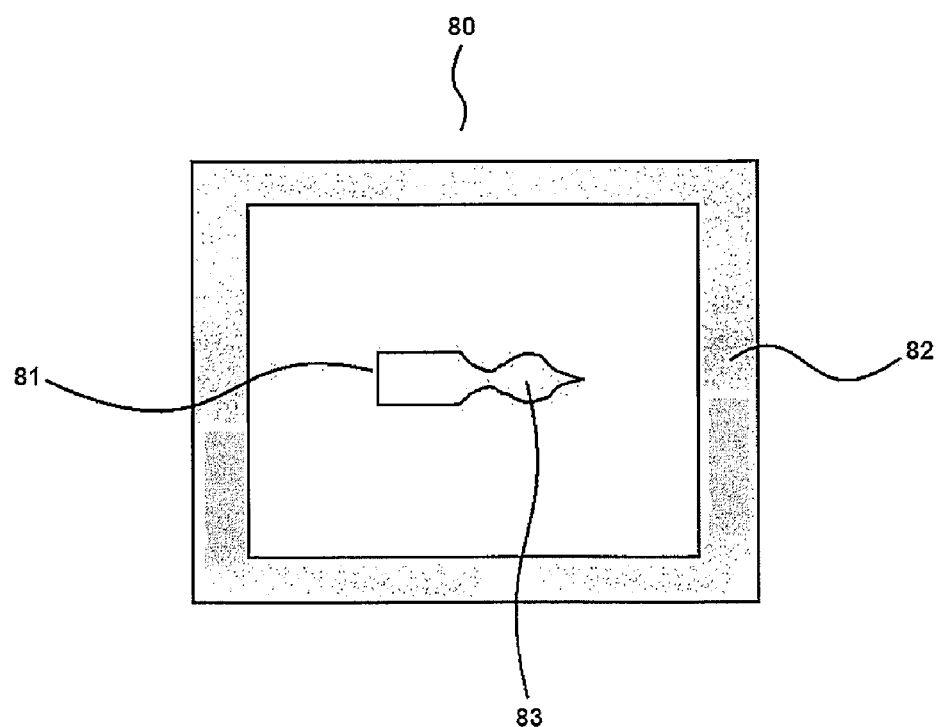
FIG. 8 illustrates another exemplary gas package.

FIG. 8 illustrates an exemplary gas package 80 wherein the sealing layer 81 defines the reservoir volume 83 and is totally or partially within the confines of the interface layer 82. In this exemplary device 80, activation is achieved by puncturing, penetrating, or otherwise causing the sealing layer 81 to open such that the internal side of the interface layer is supplied with a higher concentration or partial pressure of gas, thus resulting in a gas concentration gradient across the interface layer 82. The gas concentration gradient across the interface layer 82 results in the evolution of the gas through the interface layer. For example, in FIG. 8 the sealing layer 81 is illustrated as a glass ampoule. The glass ampoule may be activated by breaking the neck, crushing the ampoule, or otherwise causing it to rupture. Upon activation, the ampoule releases the gas contained therein, thus creating a gas concentration gradient across the interface layer 81 with a high concentration of the gas on the inside of the layer and a low concentration on the outside. The gradient in gas concentration is the driving force to evolution of the gas through the interface layer 81.

Although depicted as an ampoule, the sealing layer 81 alternatively may comprise, but is not limited to, a thin-walled pouch which can be burst by the application of external pressure; a plastic, metal, glass, or ceramic pressure cylinder or vial equipped with a penetrable seal or simple valve; a dual- or multi-chambered device that, upon rupturing, allows two or more different compounds contained in the different chambers to mix and react in order to evolve the desired gas; a single-chambered container containing a first reagent where the container is suspended in a second reagent contained within the reservoir so that, upon rupture of the container, the two reagents mix, react, and evolve the desired gas; and so forth. One of skill in the art will appreciate that many other such mechanisms can act as a reservoir to charge the internal side of the interface layer with the desired gas in accordance with the description herein.

Example 9

Figure 9A:
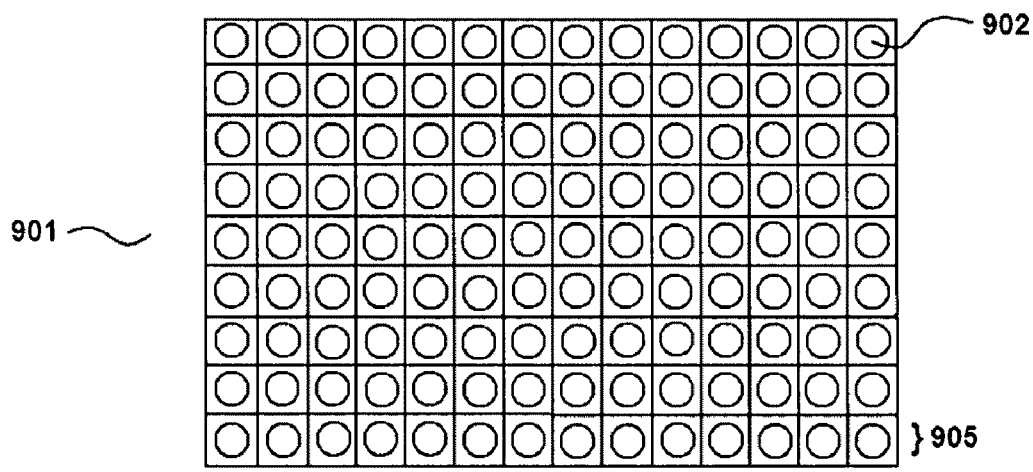
FIG. 9, embodiments A-C, illustrates another exemplary multi-reservoir gas package.
Figure 9B:
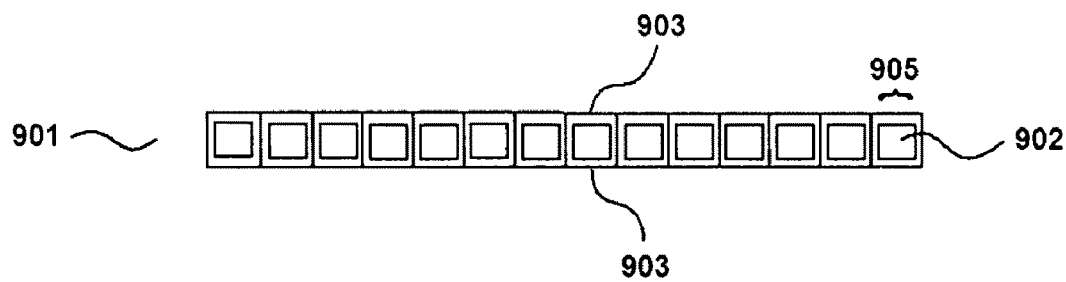

FIG. 9, embodiments A (top view) and B (side view) illustrate another exemplary multi-reservoir gas package 901 wherein the reservoirs 902 and interface layers 903 are divided into many sub units or "cells" 905 which are arranged to form a larger element. In this gas package, a small amount of gas is contained in each cell 905 and each cell 905 has one or more of its own interface layers 903. The cells can be almost any size and each cell's ratio of reservoir volume to interface layer surface area and gas concentration can be adjusted to vary the relative dose rate and duration. The gas package illustrated in FIG. 9 may comprise a variety of different cell sizes, gas concentrations, and interface layers in order to create specialized dose profiles.

Preferably, the gas package illustrated in FIG. 9, embodiments A-B, additionally comprises a sealing layer or holding container. For example, one or more sealing layers may be laminated onto one or more interface layers of the gas package with an adhesive so that the sealing layers are removable from the interface layers. Thus, the gas package can be activated by removing the sealing layer. Alternatively, or in addition to removal of the sealing layer(s), the gas package can be activated by removing it from its holding container, if provided with one.

Figure 9C:
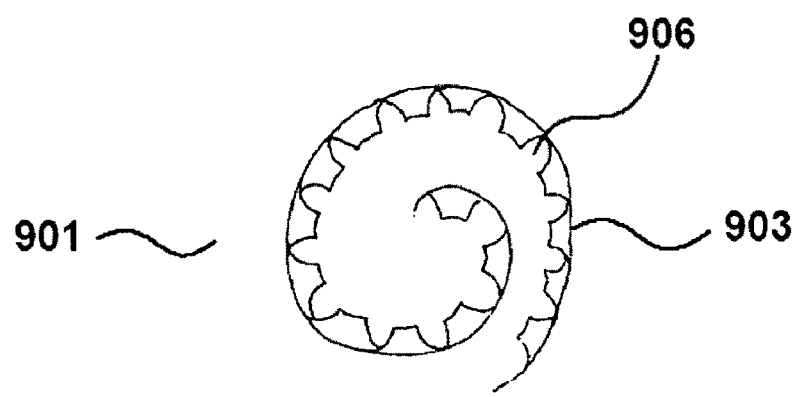

In an alternative configuration illustrated in side view in FIG. 9C, the reservoirs are embossed pockets 906 formed in a laminar structure with one or both sides of the embossed pocket forming an interface layer 903. If only one side has an interface layer, 903, the other side preferably has a sealing layer in order to confine the gas in the embossed pockets 906. Additionally, the one or more interface layers preferably are adhered to removable sealing layers, or alternatively a holding container is provided in order to prevent the evolution of gas until the device is activated, e.g., by removing one or more of the sealing layers or removing the gas package from the holding container.

In still another alternative, the gas packages may comprise tubular structures (e.g., straws) wherein the outer wall of the straw is the interface layer and the inner volume of the straw is the reservoir volume. The tubular structures may be configured into a mat-like linear array or layered with various, even random, orientations to form interstitial spaces from which the delivered gas can evolve. The tubular structure can be made of the interface layers, and can be packaged together using sealing layers. Alternatively, the gas packages configured as straws can be used individually without bundling. For example, the straw-like gas packages may be convenient for use in the administration of therapeutic gases to body orifices, such as the ear and nose. An exemplary use of the straw-like gas packages is to deliver therapeutic gases, and in particular gNO, to a body orifice to assist in healing, for example, healing the interior of the nose after a cauterization procedure is performed to close open blood vessels in the nose following a nose bleed, plastic surgery, and so forth.

Another gas package that combines some aspects of the gas packages shown in FIGS. 8 and 9 is a device with a large number of cells that are sequentially activated in a manner to produce an approximately constant evolution rate of gas. In this exemplary gas package, the individual cells may be constructed to have their characteristic delivery times somewhat longer than the time period between the activation of the next cell in the sequence. In this fashion, the net evolved gas is produced from a number of cells at various stages of discharge, which in turn may result in an approximately uniform evolution rate. Interface layers that only allow gas to pass orthogonally through the thin dimension (for example, as with thin membranes utilizing diffusion as the transport mechanism) may be advantageously used in this gas package configuration. Where this type of interface layer is used to cover a multi-reservoir cell arrangement, the relative rate of new surface exposure may determine the dose rate. This type of structure can be implemented as a laminar tape arrangement wherein the sealing layer is pulled away at a controlled rate to expose fresh gas evolving surface.

In yet a further variation, a gas package may comprise a gas-evolving interface layer that covers the highly segmented reservoir layer (for example in the manner of an embossed sheet as described previously), and a shutter that gradually exposes more of the interface layer as previously exposed areas became depleted. By varying the rate of exposure of the interface layer, the rate of gas evolution can be controlled. In another alternative, the reservoirs and interface layers may be rolled into a cylindrical structure such that the interface layer can gradually be exposed by unrolling the cylindrical structure, thus controllably evolving gas based on the unrolling rate.

Example 10

FIG. 10, embodiments A-D, illustrates gas packages 101, 102, 103, and 104 that are configured to be replacements of existing gas conditioning cartridges (e.g., conventional filters, converters, and scrubber cartridges) that are used with mouthpieces, surgical masks, face masks, and other breathing apparatuses such as the face masks illustrated. The gas packages 101, 102, 103, and 104 can be used to deliver gases to a subject's respiratory system, airway, sinuses, face, eyes, head and any combination or portion thereof. The mouthpiece, face mask, or breathing apparatus preferably may be equipped with flow directing valves to preferentially direct freshly mixed delivered gases from the gas package and breathing gases to the subject while exhausting used gases to flush out waste products and contaminants on a regular basis. Because the gas packages are configured as replacements for existing gas conditioning cartridges, the gas packages especially may be useful to augment existing personal protective equipment systems that already use replaceable gas conditioning cartridges or the like including, but not limited to: military-use gas masks; biohazardous isolation suits used in secure facilities; and protective equipment used by essential personnel such as doctors, emergency medical personnel, disaster clean up crews, and other individuals that may be exposed to contagions. The gas packages also may allow existing equipment systems to be upgraded or retrofitted such that they can deliver therapeutic gases to the respiratory system. Again, in order for the gas packages to function with existing personal protective equipment, the packages 101, 102, 103, and 104 are configured to be replacements of existing gas conditioning cartridges used in personal protective breathing equipment.

Alternatively, a smaller gas package such as those described herein may be combined with an existing gas conditioning cartridge to create a hybrid cartridge serving both functions and still otherwise compatible with the personal protective equipment. For example, the gas packages as described in reference to FIG. 1 may be sized and configured such that they are capable of being integrated within or inserted into existing gas conditioning cartridges. Upon activation of a gas package integrated with or inserted into an existing gas conditioning cartridge, the delivered gas would be mixed with the breathing air passing through the gas conditioning cartridge and delivered to the subject.

In another alternative, existing partial or full coverage protective and/or quarantine suits may be equipped with one or more gas packages integrated into the suits or attached to the interior of the suits in order to treat the body areas covered by the suits.

Gas packages configured as replacements for existing gas conditioning cartridges or as supplements of existing gas conditioning cartridges (i.e., smaller gas packages for insertion into existing gas conditioning cartridges in order to create a hybrid gas conditioning cartridge) have various military and civilian uses, especially in terms of disinfection and sterilization. For example, in the military context, the gas packages configured for replacement or augmentation of existing gas conditioning cartridges can be used to combat biological warfare agents. When the presence of a biological agent is known or suspected, a mask such as those illustrated in FIG. 10 may be worn in conjunction with a gas package either integrated into an existing gas conditioning cartridge or configured as a complete replacement for an existing gas conditioning cartridge. The gas package, by releasing the entrained therapeutic, preferably sterilizing, gas can treat incoming breathing gases in order to eliminate, or at least mitigate, the biological agents present in the gases. Preferably, the gas package is a gNO package because gNO is capable of treating infectious agents including weapons-grade bacterial and viral agents.

In the civilian context, gas packages configured as replacements for existing gas conditioning cartridges or as supplements of existing gas conditioning cartridges again may be used to prevent or combat the spread of infectious or pathogenic agents. When the presence of an infectious or pathogenic agent is known or suspected (e.g., at the site of a terrorist attack or an import/export facility like an airport, harbor, and so forth), a mask such as those illustrated in FIG. 10 may be worn in conjunction with a gas package either integrated into an existing gas conditioning cartridge or configured as a complete replacement for an existing gas conditioning cartridge. The gas package, by releasing the entrained therapeutic, preferably sterilizing, gas can treat incoming breathing gases in order to eliminate, or at least mitigate, the infectious and pathogenic agents present in the atmosphere including, but not limited to, common and exotic bacteria, viruses, and fungi such as avian (H5N1) flu, anthrax spores, and so forth.

Additionally, it is to be appreciated that the inhalation of the therapeutic gases delivered by the gas packages may treat infectious agents that already have been inhaled into the body. For example, the inhalation of gNO from a gNO package may combat the progression inside the body of an already inhaled infectious agent such as the infectious agents military and civilian health personnel might be exposed to. Thus, the gas packages described in connection with FIG. 10 not only are useful to prevent the inhalation of infectious agents by military and civilian personnel, but also may be useful to treat the effects of any infectious agents inhaled before or after use of the gas package begins. Existing gas conditioning cartridges generally lack the capability of treating the effects of already inhaled infectious agents because existing gas conditioning cartridges generally treat only incoming breathing gases and do not deliver therapeutic agents to the user. Thus, gas masks provided with gas packages as described herein may be used as treatment devices rather than merely preventative measures.

Thus, the gas packages can be advantageously used for the protection of military and civilian personnel against the spread of infectious biological agents, for example, by being integrated into existing gas conditioning cartridges used in personal protective systems or by being configured as replacements of existing gas conditioning cartridges used in personal protective systems.

In general, the gas packages described in connection with FIG. 10 are useful wherever there is a potential for inhaling pathogens or where pathogens already may have been inhaled or where pathogens already may have come into contact with the body.

Example 11

Figure 11B:
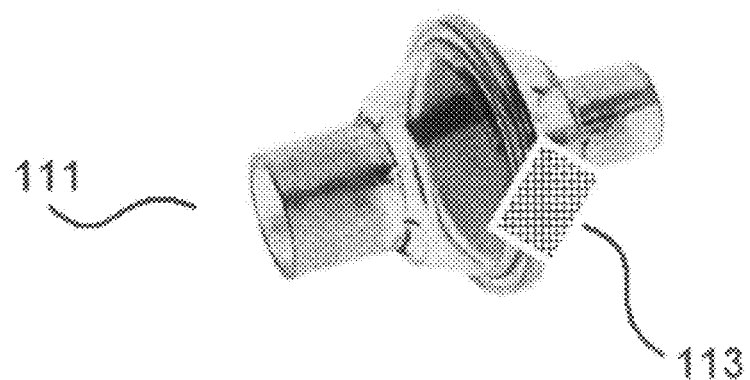
FIG. 11, embodiments A and B, illustrates a gas package implementation using a face mask. The device depicted in embodiment B alternatively can be implemented in a ventilator circuit.

FIG. 11, embodiments A and B, illustrates another gas package implementation using a mask 110 that can be placed over the face and preferably sealed to the surface of the user's face by pressure or adhesion. The mask 110 is configured so the nose and the mouth of the user are sealed separately. The mask 110 comprises a one-way valve 111 provided on the chamber which seals around the nose and a one-way valve 112 on the chamber that seals around the mouth so that the user of the gas mask can inhale through the user's nose and exhale through the user's mouth. The mask additionally comprises a gas package 113 on the inhalation side of the mask as depicted in FIG. 11, on the exhalation side of the mask, or on both the inhalation and exhalation sides of the mask. Accordingly, the mask 110 in conjunction with a gas package 113 may be used to deliver gNO or other therapeutic gases to the sinuses or respiratory system.

Alternatively, a gas mask that separates the mouth and nose through an appropriate seal on the surface of the face such that the user can breathe in only through the nose and out only through the mouth can be used in conjunction with a gas package to accomplish the same purpose of delivering therapeutic gases, for example gNO, to the user/patient.

A further use of the one-way valve 111 and the gas package 113 provided in the intake valve is for the administration of a therapeutic gas in a ventilator circuit to treat the inhaled or exhaled gases of a patient using assisted breathing. The valve 111 could be inserted into a standard ventilator circuit in order to administer one or more therapeutic gases to the ventilation gases passing through the circuit. Gas evolved from the gas package 113 is swept into the gas stream traveling through the ventilator circuit so that the breathing gas is exposed in an effective manner to the delivered gas and so that the mixing of the delivered gas with the breathing gas is complete. The one-way valve 111 can be inserted into the inhalation side of the circuit to provide a method of treating the patient. However, the valve also could be inserted into the exhalation side of the circuit, for example, to sterilize or disinfect the exhaled gases, in which case the one-way valve 111 would be oriented to allow exhalation gases to pass through the valve. In another alternative, a one-way valve with a gas package provided therein is provided on each side of the breathing circuit so that the patient receives gas treatment while the exhaled gases also are treated, optionally with a different gas profile than that of the inhaled side of the circuit.

Example 12

Figure 12A:
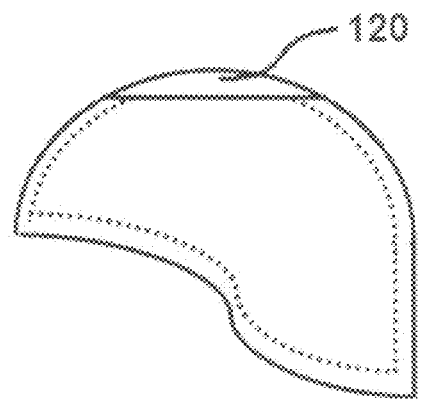
FIG. 12, embodiments A-C, illustrates a gas package used in conjunction with a shroud or enclosure.
Figure 12B:
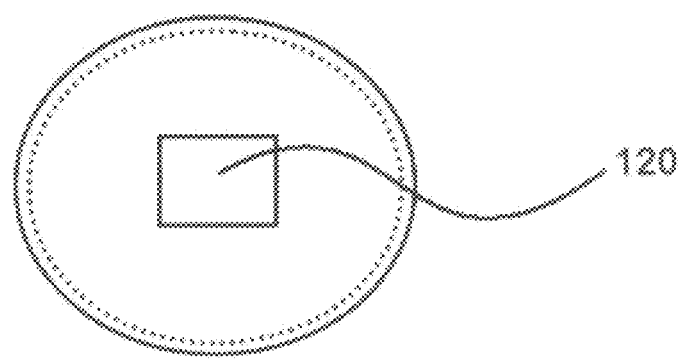
Figure 12C:
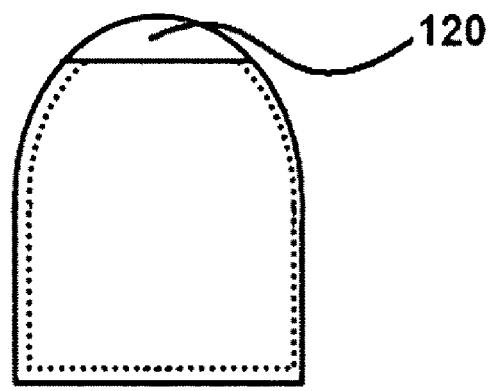

FIG. 12, embodiments A-C, illustrates another alternative use for the gas packages described herein. In FIG. 12, a gas package 120 is used in conjunction with a shroud or enclosure that surrounds an exposed area of the body that requires treatment but where it is desirable that the shroud not come into intimate contact with the patient. The gas package can be integrated into the shroud or enclosure to form part of the treatment regime or as an element to keep the shroud in a sterile field condition. An example of this configuration is shown in FIG. 12, embodiments A (side view), embodiment B (top view) and embodiment C (end view), wherein the shroud is shaped to cover a patient's scalp area and a gas package 120 is integrated into the shroud.

Alternatively, a gas package such as the gas packages described in connection with FIG. 1 can be inserted into the area or volume protected by the shroud and activated in order to release a therapeutic gas into the protected area or volume. Again, this use of the gas package may be desirable in connection with, for example, the treatment of open lesions, burns, grafts, and other large surface area sites where it is desired to leave the wound open for proper treatment but where a sterile field needs to be maintained or another therapy affected.

gNO is a preferred delivered gas for these applications because of its ability to kill pathogens.

Example 13

Figure 13:
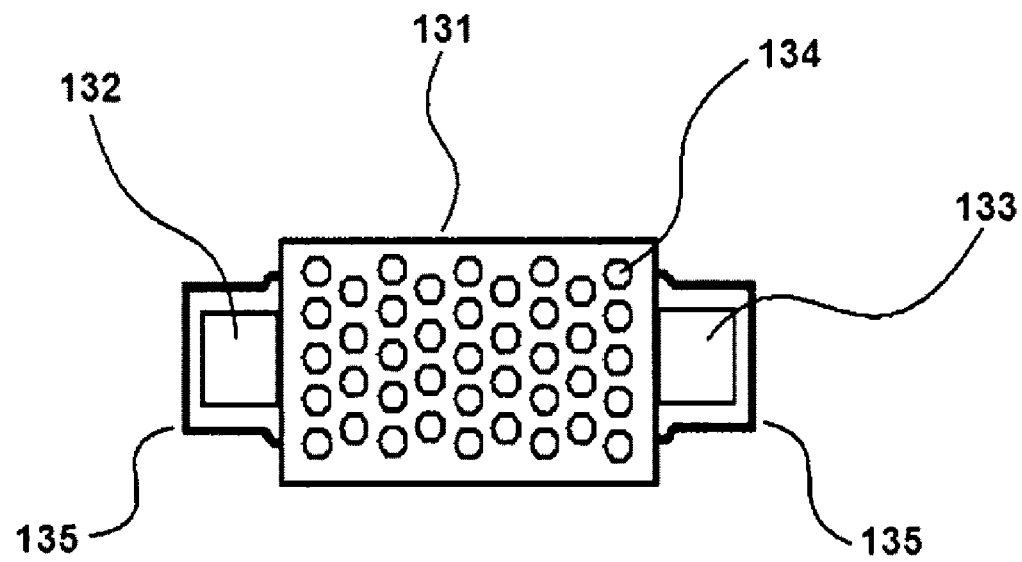
FIG. 13 illustrates a gas package comprising a holding container used as a flow element through which a fluid can pass and the delivered gas dissolved into.

FIG. 13 illustrates a gas package comprising a holding container 131 used as a flow-through element through which a fluid can pass. The ends of the flow element are sealed with caps 135 until the user wishes to insert the device into a flow circuit. Once the caps 135 are opened, the gas package is inserted into the flow circuit using the inlet tube fitting 132 and outlet tube fitting 133. Fluid flows through the gas package from inlet to outlet, passing through a bed of small beads 134. The shell of each bead is an interface layer that defines a gas reservoir from which the therapeutic gas will evolve. Such a bed of beads may have a very high surface area which may allow the circulating fluid to contact the delivered gas in an effective manner. For instance, the gas packages can comprise a packed or loose bed of beads, a bonded conglomerate of beads (similar to a foam structure), a rolled-up or folded laminar structure (see explanation of FIG. 9), a bundle of tubes or straws (see explanation of FIG. 9), or any of a number of other comparable arrangements that allow the fluid to pass in close proximity to the interface layers that evolve gas and thus allow the fluid to be effectively exposed to the delivered gas.

Fluids that could be processed in this manner include, but are not limited to: process liquids that need to be sterilized or disinfected such as formulations that are administered to a patient; body fluids such as blood; waste fluids that might be contaminated; and air, such as room air, that is being inhaled or exhaled (in the case of inhalation the gas might be targeted for treatments to the lungs and in the case of exhalation, the gas might be intended to kill pathogens that might be present in the exhaled breath). In the case of treating blood, the gas package can be incorporated into a prefabricated circuit such as those common in blood collection, processing, and infusion applications. Treatment of circulating blood with, for example, gNO may be desired for platelet deactivation, inhibiting or killing pathogens such as viruses and bacterium, inducing biofilm reduction, and to produce other known effects caused by the application of gNO directly to the blood.

The gas package illustrated in FIG. 13 alternatively can be inserted as a flow-through element in a ventilator circuit to treat the inhaled or exhaled gases of a patient using assisted breathing. Gas evolved from the reservoir through the interface layer is swept into the gas stream traveling through the ventilator circuit so that the breathing gas is exposed in an effective manner to the delivered gas and so that the mixing of the delivered gas with the breathing gas is complete. The gas package can be inserted into the inhalation side of the circuit to provide a method of treating the patient; the gas package can be inserted into the exhalation side of the circuit, for example, to sterilize or disinfect the exhaled gases. In another alternative, a gas package is provided on each side of the breathing circuit so that the patient receives gas treatment while the exhaled gases also are treated, optionally with a different gas profile than that of the inhaled side of the circuit.

In another configuration applicable to treating fluids, including blood, an interface layer is provided within a structure that forces a thin sheet of the fluid to flow against the interface layer so that there is a high degree of exposure between the fluid and the interface layer. For example, a filter layer found in structures that are used in blood filtering applications can be substituted with an appropriate interface layer with one or more reservoirs on the side of the interface layer away from the blood.

Example 14

The gas packages described herein also can used for decontamination and/or containment purposes. For example, a suitable gas package may be placed inside of or included within a durable bag provided with an airtight zipper, sealing strip, or other similar closure mechanism. The bag may be used to collect or store contaminated material. In use, the bag can be sealed so that the contaminated material is immersed in an atmosphere rich in the delivered gas originating from an activated gas package. A gas package incorporated into a sealable bag may be useful, for example, for sterilizing or fumigating soiled linens, treating medical waste, and other similar applications. A specialized gas package and bag combination is a "body bag" wherein a corpse or other material considered contagious is placed for sterilization while in storage or awaiting transport, disposal, or other disposition.

In order to sterilize or fumigate a large volume, the gas package may function similarly to a smoke generator canister or grenade such that once activated, the gas package produces a large rapid release of gas to fumigate buildings, rooms, vehicles, and similar enclosures that may have become contaminated. The gas package configured as a smoke generator canister or grenade may be tossed or placed in a contaminated volume or enclosure, for instance a room, after a triggering or fusing mechanism is activated in order to provide a specified delay period before gas is released.

The above are only a small selection of the possible configurations and associated applications of the gas packages that are envisioned. Many other configurations and applications of the gas packages also are possible in accordance with the description herein, depending upon the desired dose profiles, physical constraints, and the specific needs of the many end applications to which the devices can be applied. The gas packages therefore may be implemented in many suitable forms and the various components may be physically or functionally varied to meet the need of different applications.

The foregoing detailed description is provided solely to describe the invention in detail, and is not intended to limit the invention. Those skilled in the art will appreciate that various modifications may be made to the invention without departing significantly from the spirit and scope thereof.

We claim:

1. A method of administering one or more therapeutic gases to an animal or human patient, comprising:
    providing at least one device comprising a reservoir that is capable of supplying the one or more therapeutic gases, an interface layer, made of a gas permeable material surrounding the reservoir, through which the gases must transit in order to reach the patient,
    and an element, covering all or some of the interface layer, that prevents the flow of therapeutic gases through the interface layer to the patient until the at least one device is activated, and that is selected from the group consisting of a sealing layer, a holding container, and combinations thereof;
    activating the at least one device by compromising the element; and
    allowing the one or more therapeutic gases to transit from the reservoir through the interface layer to the patient.

2. The method of claim 1, wherein the one or more therapeutic gases are selected from the group consisting of gaseous nitric oxide (gNO), oxygen ($O_2$), carbon monoxide (CO), nitrogen ($N_2$), and nitrous oxide ($N_2O$).

3. The method of claim 2, wherein the one or more therapeutic gases is gaseous nitric oxide (gNO).

4. The method of claim 1, further comprising selecting the interface layer on the basis of one or more factors selected from the group consisting of the partial pressure of therapeutic gases in the reservoir, the concentration of the one or more therapeutic gases in the reservoir, and a desired delivery rate of the one or more therapeutic gases to the animal or human patient.

5. The method of claim 1, wherein the one or more therapeutic gases are administered to a situs on or in the animal or human patient selected from the group consisting of the mouth, teeth, gums, anus, vagina, nose, ears, eyes, and skin.

6. The method of claim 1, wherein the one or more therapeutic gases are administered into a protective suit and subsequently inhaled by the animal or human patient.

7. The method of claim 1, wherein the one or more therapeutic gases are administered into a protective suit and subsequently absorbed into the animal or human patient's skin.

8. The method of claim 1, wherein the one or more therapeutic gases are administered into a breathing apparatus and subsequently inhaled by the animal or human patient.

9. The method of claim 1, wherein the one or more therapeutic gases treat a disease or non-disease state in the animal or human patient selected from the group consisting of: vasodilatation; bacterial, viral, and fungal infections; biofilms; respiratory conditions; respiratory, airway, eye, and ear infections;
    wound infections; burns; cancer; cosmetic conditions; topical conditions; skin and tissue conditions; blood conditions; inflamation; bronchoconstriction; reversible pulmonary vasoconstriction; asthma; pulmonary hypertension; adult respiratory distress syndrome (ARDS); and persistent pulmonary hypertension of the newborn (PPHN).

10. The method of claim 1, wherein the one or more therapeutic gases prevent a disease or non-disease state in the animal or human patient selected from the group consisting of vasodilatation; bacterial, viral, and fungal infections; biofilms; respiratory conditions; respiratory, airway, eye, and ear infections; wound infections; burns; cancer; cosmetic conditions; topical conditions; skin and tissue conditions; blood conditions; inflammation; bronchoconstriction; reversible pulmonary vasoconstriction; asthma; pulmonary hypertension; adult respiratory distress syndrome (ARDS); and persistent pulmonary hypertension of the newborn (PPHN).

11. A method of treating or preventing disease and non-disease states in an animal or human patient, comprising administering one or more therapeutic gases to the patient by activating one or more gas package devices, wherein at least one gas package device comprises:
    a reservoir that is capable of supplying the one or more therapeutic gases;
    an interface layer, made of a gas permeable material surrounding the reservoir, that regulates the flow of the one or more therapeutic gases from the reservoir to an environment external to the at least one device; and
    an element, covering all or some of the interface layer, that prevents the flow of therapeutic gases through the interface layer to the external environment until the at least one device is activated by compromising the element, and that is selected from the group consisting of a sealing layer, a holding container, and combinations thereof.

12. The method of claim 11, wherein the disease and non-disease states are selected from the group consisting of: vasodilatation; bacterial, viral, and fungal infections; biofilms; respiratory conditions; respiratory, airway, eye, and ear infections; wound infections; burns; cancer; cosmetic conditions; topical conditions; skin and tissue conditions; blood conditions; inflammation; bronchoconstriction; reversible pulmonary vasoconstriction; asthma; pulmonary hypertension; adult respiratory distress syndrome (ARDS); and persistent pulmonary hypertension of the newborn (PPHN).

13. The method of claim 11, wherein the one or more therapeutic gases are selected from the group consisting of gaseous nitric oxide (gNO), oxygen ($O_2$), carbon monoxide (CO), nitrogen ($N_2$), and nitrous oxide ($N_2O$).

14. The method of claim 13, wherein the one or more therapeutic gases is gaseous nitric oxide (gNO).

15. The method of claim 11, wherein the one or more therapeutic gases is delivered to a situs on or in the animal or human patient selected from the group consisting of the skin, respiratory airways, upper nasal system, sinuses, eyes, rectum, vagina, face, and mouth.

* * * * *